United States Patent
Okabe et al.

(10) Patent No.: US 10,290,131 B2
(45) Date of Patent: May 14, 2019

(54) TIME SERIES DATA DISPLAY CONTROL DEVICE, METHOD FOR OPERATING THE SAME, PROGRAM, AND SYSTEM

(71) Applicant: FUJIFILM Corporation, Tokyo (JP)

(72) Inventors: Yuuki Okabe, Tokyo (JP); Yasuyo Nenoki, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 54 days.

(21) Appl. No.: 15/498,496

(22) Filed: Apr. 27, 2017

(65) Prior Publication Data

US 2017/0228900 A1 Aug. 10, 2017

Related U.S. Application Data

(63) Continuation of application No. PCT/JP2015/077649, filed on Sep. 30, 2015.

(30) Foreign Application Priority Data

Nov. 21, 2014 (JP) ................................. 2014-237155

(51) Int. Cl.
*G06T 11/20* (2006.01)
*A61B 5/00* (2006.01)
(Continued)

(52) U.S. Cl.
CPC ............ *G06T 11/206* (2013.01); *A61B 5/743* (2013.01); *A61B 5/7435* (2013.01); *G06F 17/18* (2013.01); *G06T 3/00* (2013.01); *G06T 15/20* (2013.01); *G06F 19/321* (2013.01); *G06F 19/324* (2013.01); *G06T 3/60* (2013.01);
(Continued)

(58) Field of Classification Search
None
See application file for complete search history.

(56) References Cited

U.S. PATENT DOCUMENTS

| | | | | |
|---|---|---|---|---|
| 8,502,821 B2* | 8/2013 | Louise | ............... | G01R 13/0236 345/419 |
| 8,730,243 B2 | 5/2014 | Wenholz et al. | | |
| 2005/0234670 A1* | 10/2005 | Hagen | .................. | G01R 13/206 702/85 |

FOREIGN PATENT DOCUMENTS

| | | |
|---|---|---|
| JP | H06-243264 | 9/1994 |
| JP | 2009-031930 | 2/2009 |
| JP | 2012-148079 | 8/2012 |

OTHER PUBLICATIONS

Stack Overflow, "Ignore cells on Excel line graph", https://stackoverflow.com/questions/18317924/ignore-cells-on-excel-line-graph, 2013. (Year: 2013).*

(Continued)

*Primary Examiner* — Nicholas R Wilson
(74) *Attorney, Agent, or Firm* — JCIPRNET

(57) ABSTRACT

A main display region 41 in which medical care data on a plurality of items is displayed is provided on a display screen 15. The main display region 41 may be displayed in two display modes of a two-dimensional display mode and a three-dimensional display mode in which a time scale is longer than a time axis of the two-dimensional display mode and a two-dimensional plane on which time series data is displayed is three-dimensionally displayed using the laws of perspective by which a plurality of straight lines parallel to the time axis in the two-dimensional display mode are drawn to be converged toward the past on the time axis.

16 Claims, 13 Drawing Sheets

(51) Int. Cl.
  *G06T 15/20*   (2011.01)
  *G06T 3/00*    (2006.01)
  *G06F 17/18*   (2006.01)
  *G16H 40/63*   (2018.01)
  *G06F 19/00*   (2018.01)
  *G06T 3/60*    (2006.01)
  *G06T 11/60*   (2006.01)
  *H04L 29/06*   (2006.01)

(52) U.S. Cl.
  CPC .............. *G06T 11/60* (2013.01); *G16H 40/63* (2018.01); *H04L 67/42* (2013.01)

(56) References Cited

OTHER PUBLICATIONS

John Peltier, "Excel 3D Charts: Charts with No Value", https://peltiertech.com/excel-3d-charts-with-no-value/, 2011. (Year: 2011).*

"Office Action of Japan Counterpart Application," dated Nov. 22, 2017, with English translation thereof, p. 1-p. 7.

"International Search Report (Form PCT/ISA/210) of PCT/JP2015/077649", dated Dec. 1, 2015, with English translation thereof, pp. 1-2.

"Written Opinion of the International Searching Authority (Form PCT/ISA/237) of PCT/JP2015/077649", dated Dec. 1, 2015, with English translation thereof, pp. 1-11.

\* cited by examiner

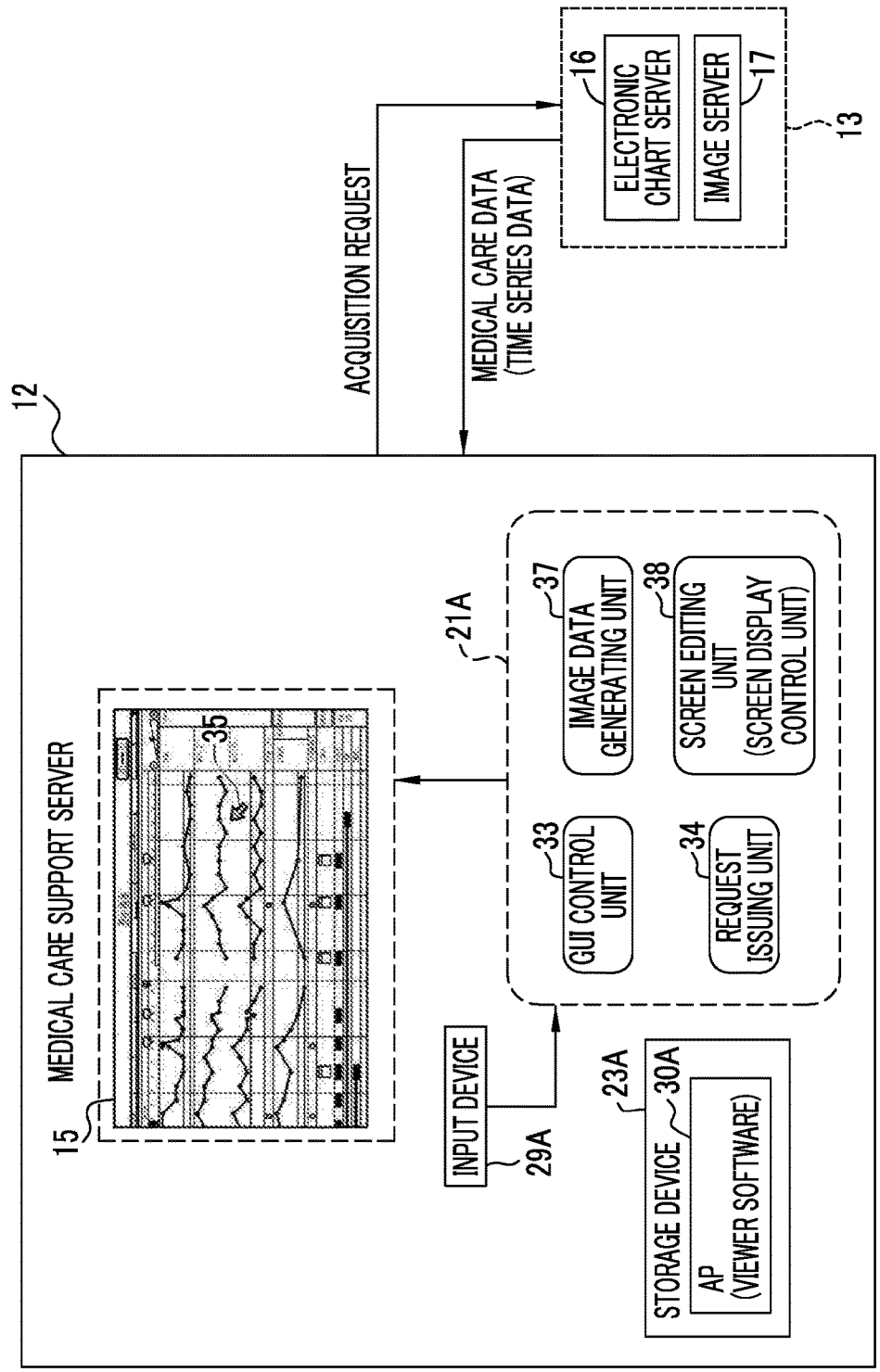

TIME SERIES DATA DISPLAY CONTROL DEVICE, METHOD FOR OPERATING THE SAME, PROGRAM, AND SYSTEM

CROSS-REFERENCE TO RELATED APPLICATIONS

This application is a Continuation of PCT International Application No. PCT/JP2015/077649 filed on Sep. 30, 2015, which claims priority under 35 U.S.C § 119(a) to Patent Application No. 2014-237155 filed in Japan on Nov. 21, 2014, all of which are hereby expressly incorporated by reference into the present application.

BACKGROUND OF THE INVENTION

1. Field of the Invention

The present invention relates to a time series data display control device, a method for operating the same, a program, and a system.

2. Description of the Related Art

Devices that display time series data indicating time-dependent changes in data have been used in various fields. For example, JP2012-148079A discloses a device that displays time series data indicating time-dependent changes in data on medical care, such as a blood pressure, a body temperature or a heart rate of a patient, on a display screen in a medical field (JP2012-148079A). The time series data is two-dimensionally displayed, for example, on a two-dimensional plane formed by a time axis and an array axis orthogonal to the time axis for arraying a plurality of pieces of time series data (FIG. 4). Further, a display device disclosed in JP1994-243264A (JP-H6-243264A) shows a technique that three-dimensionally displays time series data. More specifically, a longitudinal direction of a virtual cylinder is set as a time axis, and a plurality of pieces of time series data are allocated to a circumferential surface thereof. Further, the plurality of pieces of time series data are displayed in such a form that observation is performed with a point of view being inside the virtual cylinder and with eyes being directed along the longitudinal direction (<0014> to <0017>, and FIG. 5).

In JP1994-243264A (JP-H6-243264A), the virtual cylinder is set as an allocation region of the plurality of pieces of time series data for the purpose of reducing overlap of the plurality of pieces of time series data. That is, in a case where the plurality of pieces of time series data are two-dimensionally displayed, an array axis direction orthogonal to the time axis and a direction in which values of time series data vary overlap each other. Thus, if the data fluctuation is large, the plurality of pieces of time series data overlap each other, which makes it hard to see the data. In order to handle this problem, in JP1994-243264A (JP-H6-243264A), by setting the virtual cylinder, it is possible to reduce the overlap of the plurality of pieces of time series data by enlarging the allocation region of the plurality of pieces of time series data in comparison with the two-dimensional plane.

In the three-dimensional display disclosed in FIG. 5 of JP1994-243264A (JP-H6-243264A), the plurality of pieces of time series data allocated to the circumferential surface of the virtual cylinder are radially displayed from the center of the cylinder. Further, in the above-described three-dimensional display, using a screen scroll operation, the time axis can be scrolled, and enlargement display or reduction display of the time series data can also be performed.

SUMMARY OF THE INVENTION

However, for example, since time series data relating to medical care has the following characteristics, only the two-dimensional display technique disclosed in JP2012-148079A or the three-dimensional display technique disclosed in JP1994-243264A (JP-H6-243264A) are not sufficient, and there is room for improvement.

According to patients, there is a case where a medical care is performed over a long period, or is a case where a patient repeatedly enters and leaves a hospital to receive an intermittent medical care. In such a case, with respect to time series data relating to the medical care, an acquisition period of the time series data becomes long. It is natural that time series data over a long period has a long time axis. The time series data relating to the medical care is used by a doctor for use in determining a medical care policy of a patient. In determination of the medical care policy, since it is important to recognize both of the presence or absence of a short-term change of time series data relating to a medical care or details thereof and an overall tendency over a long period, a technique for easily recognizing the both is necessary.

Further, since a screen size of a display on which time series data is displayed is finite, there is also a limit in a displayable period of long-term time series data due to a visually recognizable size of the time series data. For this reason, it is general that a part of the entire time period is displayed and the remaining non-display part is able to be displayed by a screen scroll operation as disclosed in JP1994-243264A (JP-H6-243264A). However, in a case where the long-term time series data is viewed by the screen scroll operation, the time axis becomes longer, and thus, an operation amount of the screen scroll increases. Thus, the operation is complicated.

Further, since the screen scroll operation is nothing but an operation of exchanging the display part and the non-display part of the time series data, there is an aspect that it is difficult to recognize the tendency by overlooking the long-term time series data. Such an aspect becomes prominent as the time axis becomes longer. JP2012-148079A and JP1994-243264A (JP-H6-243264A) do not disclose nor suggest any such problem or solution.

An object of the invention is to provide a time series data display control device, a method for operating the same, a non-transitory computer readable recording medium storing a program, and a system capable of recognizing both of the presence or absence of a short-term change of time series data or details thereof and an overall tendency over a long period with a simple operation.

In order to solve the above problems, according to an aspect of the invention, there is provided a time series data display control device including a screen data generating unit and a screen display control unit. The screen data generating unit generates a time series data display screen on which a plurality of pieces of time series data are displayed. The screen display control unit performs switching between display modes of the time series data display screen, in which the display modes include two display modes of a two-dimensional display mode in which the time series data is displayed on a two-dimensional plane formed by two axes of a time axis of the plurality of pieces of time series data and a data array axis orthogonal to the time axis, on which the plurality of pieces of time series data are arrayed, and a three-dimensional display mode in which a time scale is set to be longer than a time axis of the two-dimensional display mode and the two-dimensional plane is three-dimensionally displayed using the laws of perspective by which a plurality of straight lines parallel to the time axis in the two-dimensional display mode are drawn to be converged toward the past on the time axis.

It is preferable that the three-dimensional display mode is a display mode in which the two-dimensional plane in the two-dimensional display mode is virtually rotated around a rotation axis orthogonal to the time axis. It is preferable that a rotation angle of the two-dimensional plane is changeable. It is preferable that the time scale of the time axis becomes longer as the rotation angle becomes larger.

It is preferable that in the two-dimensional display mode, a transverse axis of the time series data display screen is set as the time axis and a longitudinal axis thereof is set as the data array axis, and in the three-dimensional display mode, the rotation axis and the longitudinal axis coincides with each other.

It is preferable that the time series data display screen includes two time axes of a first time axis which is two-dimensionally displayed similar to the two-dimensional display mode even in the three-dimensional display mode, and a second time axis which is provided in the two-dimensional plane on which the time series data is displayed and is three-dimensionally displayed similar to the two-dimensional plane, and a display period of the first time axis is changed in conjunction with a display period of the second time axis which is changed depending on the rotation angle of the two-dimensional plane.

It is preferable that in the three-dimensional display mode, a part of a display period of the time series data is able to be two-dimensionally displayed.

It is preferable that in the three-dimensional display mode, an item name display region for displaying respective item names of the plurality of pieces of time series data is two-dimensionally displayed.

It is preferable that on the time series data display screen, the item name display region is disposed at an end in a current direction on the time axis.

It is preferable that on the time series data display screen, a period during which the time series data does not exist is compressed in the time axis direction to be displayed.

It is preferable that the time series data is medical care data relating to a medical care of a patient.

According to another aspect of the invention, there is provided a method for operating a time series data display control device, including a screen data generating step and a screen display control step. The screen data generating step is a step of generating a time series data display screen on which a plurality of pieces of time series data are displayed. The screen display control step is a step of performing switching between display modes of the time series data display screen, in which the display modes include two display modes of a two-dimensional display mode in which the time series data is displayed on a two-dimensional plane formed by two axes of a time axis of the plurality of pieces of time series data and a data array axis orthogonal to the time axis, on which the plurality of pieces of time series data are arrayed, and a three-dimensional display mode in which a time scale is set to be longer than a time axis of the two-dimensional display mode and the two-dimensional plane is three-dimensionally displayed using the laws of perspective by which a plurality of straight lines parallel to the time axis in the two-dimensional display mode are drawn to be converged toward the past on the time axis.

According to still another aspect of the invention, there is provided a non-transitory computer readable recording medium storing a time series data display control program that causes a computer to function as a time series data display control device, including a screen data generating step and a screen display control step. The screen data generating step is a step of generating a time series data display screen on which a plurality of pieces of time series data are displayed. The screen display control step is a step of performing switching between display modes of the time series data display screen, in which the display modes include two display modes of a two-dimensional display mode in which the time series data is displayed on a two-dimensional plane formed by two axes of a time axis of the plurality of pieces of time series data and a data array axis orthogonal to the time axis, on which the plurality of pieces of time series data are arrayed, and a three-dimensional display mode in which a time scale is set to be longer than a time axis of the two-dimensional display mode and the two-dimensional plane is three-dimensionally displayed using the laws of perspective by which a plurality of straight lines parallel to the time axis in the two-dimensional display mode are drawn to be converged toward the past on the time axis.

According to still another aspect of the invention, there is provided a time series data display control system including a screen data generating unit and a screen display control unit. The screen data generating unit generates a time series data display screen on which a plurality of pieces of time series data are displayed. The screen display control unit performs switching between display modes of the time series data display screen, in which the display modes include two display modes of a two-dimensional display mode in which the time series data is displayed on a two-dimensional plane formed by two axes of a time axis of the plurality of pieces of time series data and a data array axis orthogonal to the time axis, on which the plurality of pieces of time series data are arrayed, and a three-dimensional display mode in which a time scale is set to be longer than a time axis of the two-dimensional display mode and the two-dimensional plane on which the time series data is displayed is three-dimensionally displayed using the laws of perspective by which a plurality of straight lines parallel to the time axis in the two-dimensional display mode are drawn to be converged toward the past on the time axis.

According to the invention, it is possible to recognize both of the presence or absence of a short-term change or details thereof and an overall tendency over a long period with respect to time series data using a simple operation.

BRIEF DESCRIPTION OF THE DRAWINGS

FIG. 4 is a block diagram showing a configuration of a computer used in a medical care support server or the like.

FIG. 14 is a diagram illustrating a client terminal according to a third embodiment.

DESCRIPTION OF THE PREFERRED EMBODIMENTS

[First Embodiment]

Figure 1:
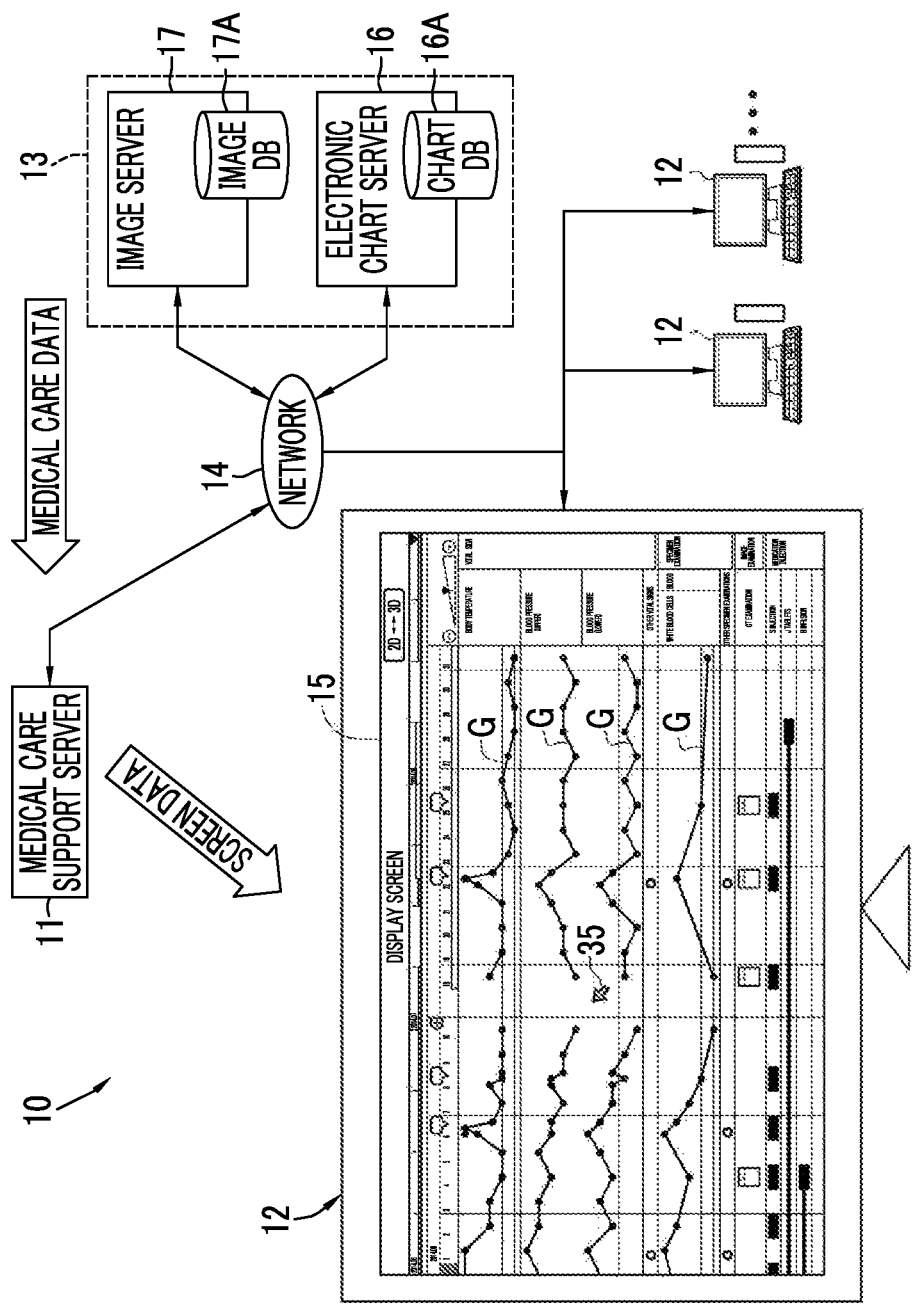
FIG. 1 is a diagram illustrating a medical information system.

A medical information system 10 shown in FIG. 1 is a computer system used for managing and using medical information at medical facilities such as hospitals. The medical information system 10 includes a medical care support server 11 which is a first embodiment of a time series data display control device of the invention, a client terminal 12, a server group 13, and a network 14 that connect these devices for communication.

The server group 13 represents servers that store medical care data of a patient. The server group 13 includes an electronic chart server 16, an image server 17, and the like. The network 14 is a local area network (LAN) provided in a hospital, for example.

The client terminal 12 is a terminal provided in each medical department such as internal medicine, surgery, otolaryngology, or ophthalmology, and is operated by a doctor in the medical department, for example. The client terminal 12 has a function of accessing the electronic chart server 16 to input or view an electronic chart. In the electronic chart, medical care data including diagnosis records such as inquiries and diagnosis content, measurement values of medical examination and measured values of vital signs, or treatment records such as treatment or surgery is input. Further, the client terminal 12 has a function of accessing the image server 17 to view examination images such as X-ray images. In this way, the client terminal 12 functions as a viewer terminal for viewing medical care data.

Further, the client terminal 12 accesses the medical care support server 11 to receive distribution of screen data on a time series data display screen (hereinafter, referred to as a display screen) 15 that displays time series data indicating time-dependent changes of medical care data of a patient, and displays the distributed display screen 15. The display screen 15 is able to collectively display examination values or measurement values in medical examination included in an electronic chart and examination images in one screen, unlike a chart display screen exclusive for the electronic chart or an image display screen exclusive for the examination images. On the display screen 15, time series data indicating time-dependent changes of the examination values or the measurement values is displayed in the form of a polygonal line graph G, for example.

The medical care support server 11 receives a distribution request of medical care data including patient designation from the client terminal 12. The medical care support server 11 acquires medical care data of a designated patient from the electronic chart server 16 or the image server 17 on the basis of the distribution request. The medical care support server 11 generates screen data for the display screen 15 on the basis of the acquired medical care data, and distributes the screen data to the client terminal 12 which is a request source. Further, the medical care support server 11 has a function of editing screen data according to the request from the client terminal 12 to perform a screen display control of the display screen 15, and functions as a time series data display control device of the invention.

The electronic chart server 16 includes an electronic chart database (hereinafter, referred to as a chart database (DB)) 16A in which an electronic chart is stored. The image server 17 includes an image DB 17A in which a plurality of examination images are stored, and is a so-called a picture achieving and communication system (PACS) server. The chart DB 16A and the image DB 17A are databases capable of being retrieved using keywords such as patient identification data (ID).

Figure 2:
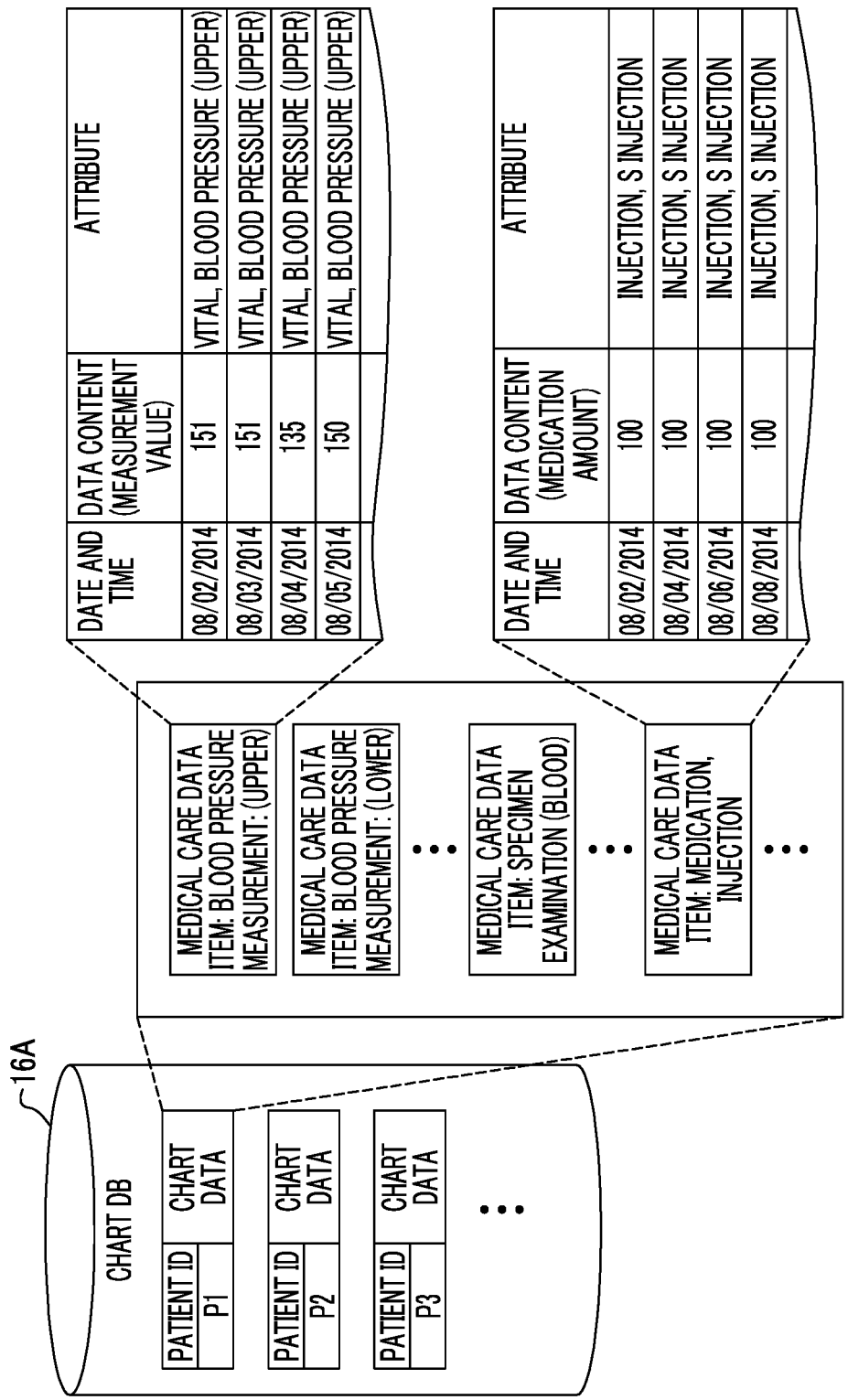
FIG. 2 is a diagram illustrating medical care data recorded in an electronic chart.

As shown in FIG. 2, the chart DB 16A stores chart data in which medical care data of a patient is stored. The chart data is assigned patent ID (P1, P2, . . . ) and is managed in the unit of patients. The chart data includes basic patient information such as a name, a birthday, a gender and a patient ID of a patient, and medical care data of the patient.

The medical care data includes measurement values of vital signs such as a heartbeat, a pulse rate, a blood pressure, and a body temperature of a patient, and examination values of clinical examinations performed for the patient. The clinical examinations include specimen tests such a blood test or a biochemical test, and electroencephalography examinations such as a physiological test. In addition, the medical care data includes details of medical treatment given to the patient, specifically, content of treatment such as medication, injection, surgery or treatment, content of inquiries. In this way, a plurality of items are included in the medical care data, and in FIG. 2, as the medical care data, items such as measurement values of a blood pressure (upper) and a blood pressure (lower), examination values of a sample examination (blood test), or injection dosages of S injection.

A record of one item among the respective items of the medical care data includes information on dates and times such as examination dates or measurement dates, content of acquired data (examination value or measurement value), and attributes thereof. The information on dates and times indicates measurement dates and times if it relates to measurement values, indicates examination dates and times if it relates to examination values, and indicates medication or injection dates and times or medicine prescription date and times if it relates to medication or injection. Since medication may take a period of time until an effect appears, for example, medication (taking medicine) over a predetermined period of time, such as "take a certain dose everyday for 5 days", may be instructed by one-time prescription. In this case, as the medication time and date, the date and time scheduled to be taken is recorded.

The attributes represent information given for sorting of data, and represent information indicating attributes of each item of the medical care data. The attributes may also be used as keywords for retrieval of the medical care data. The attributes include an item name ("blood pressure (upper)" or the like) of the medical care data, a category to which an item belongs ("vital"), and the like, for example. In addition to an item name "injection", a medication name "S" injection liquid", for example, may be given to an item of medication or injection.

Figure 3:
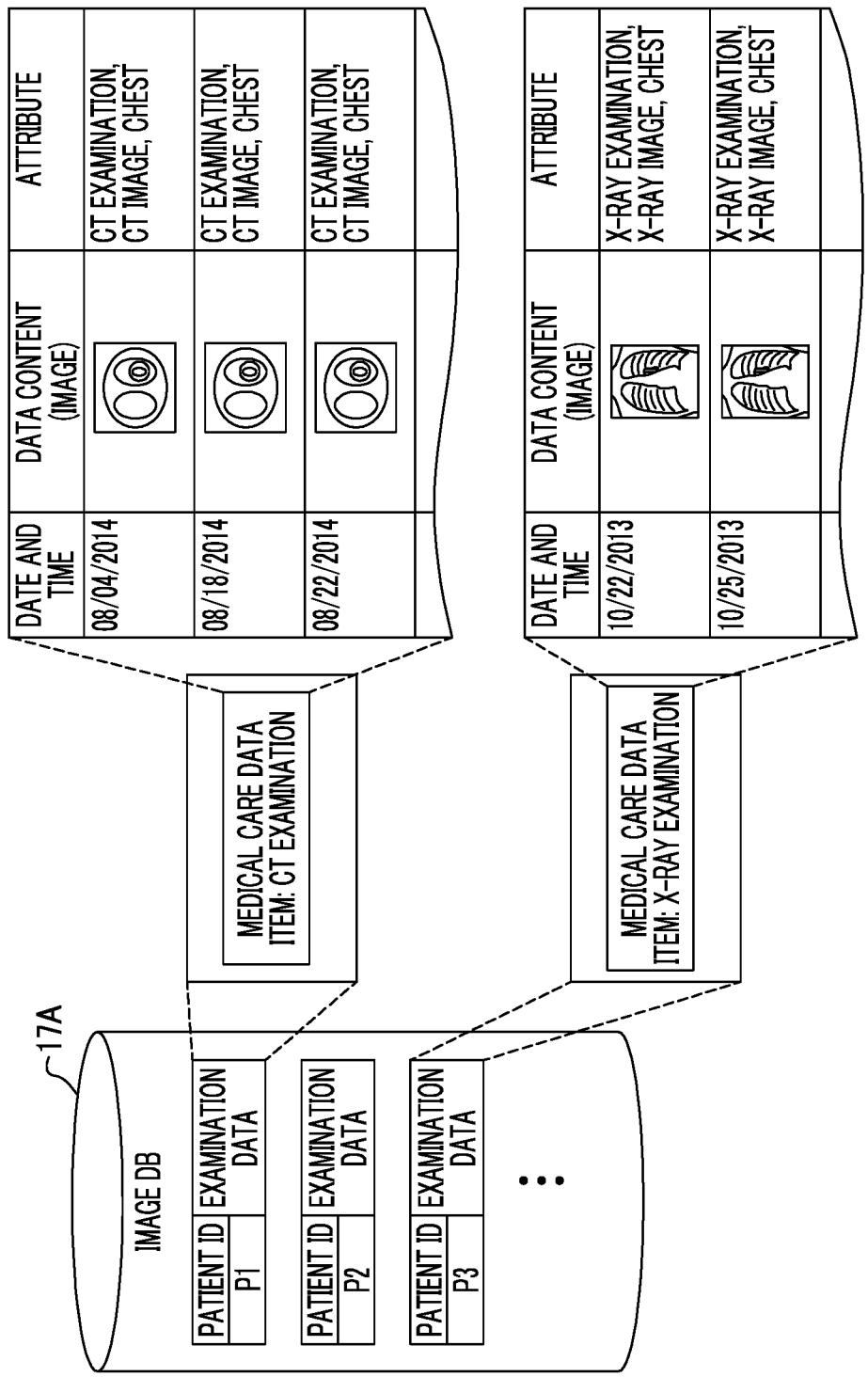
FIG. 3 is a diagram illustrating medical care data recorded in an image server.

As shown in FIG. 3, the image DB 17A stores examination data formed by a plurality of examination images captured in image examination such as X-ray examination or CT examination. A patient ID is given to the examination images, and the examination images may be retrieved using the patient ID. In the image examination, a plurality of examination images may be captured by one examination like a plurality of tomographic images acquired in CT examination. The same examination ID may be given to a plurality of examination images acquired by one examination and may be managed as a one-time examination image. Further, the examination images may be managed every date and time when the image examination is performed.

In addition, content of data of an examination image may include image analysis information obtained by analyzing the examination image, in addition to data on the examination image. The image analysis information may include, for example, information on the size of a lesion in the examination image and the type of the lesion. The image analysis information may be information calculated by image processing, or may be input information of content determined by a doctor based on image observation. The attributes of the examination image include information indicating "X-ray examination", "CT examination" indicating an examination type, "X-ray image" or "CT image" indicating an image type, "chest" or "head" indicating a photographed portion, for example.

The medical care support server 11, the client terminal 12, the electronic chart server 16, and the image server 17 are configured by installing a control program such as an operating system, and an application program such as a client program or a server program in a computer such as a personal computer, a server computer or a workstation, which is a base.

Figure 4:
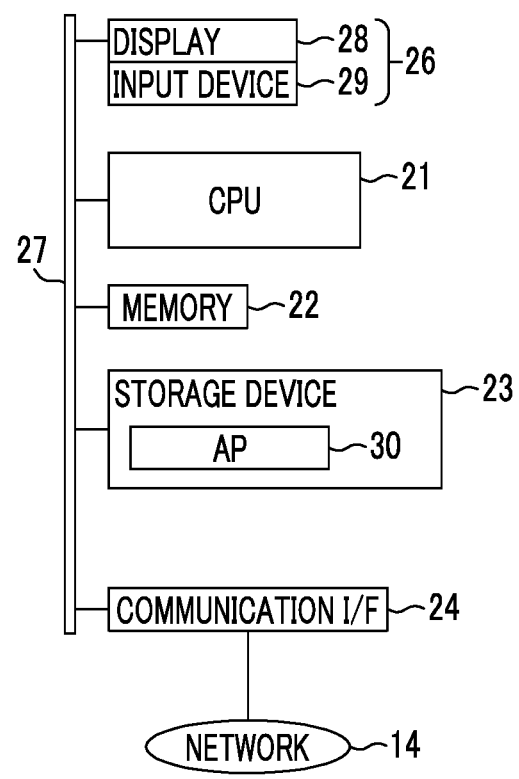

As shown in FIG. 4, computers that configures the respective servers 11, 16, and 17 and the client terminal 12 are the same in basic configurations, and each of the computers includes a central processing unit (CPU) 21, a memory 22, a storage device 23, a communication I/F 24, and an input/output unit 26. These components are connected to each other through a data bus 27. The input/output unit 26 includes a display (display unit) 28, and an input device 29 such as a keyboard or a mouse.

The storage device 23 is, for example, a hard disk drive (HDD), and stores a control program or an application program (hereinafter, referred to as an AP) 30. Further, for example, a disk array in which a plurality of HDDs are continuously provided is provided as the storage device 23 for a DB in a server in which the DB is built, in addition to the HDD that stores the program. The disk array may be provided in a main body of the server, or may be provided separately from the main body of the server and may be connected to the main body of the server through a cable or a network.

The memory 22 is a work memory for execution of processes of the CPU 21, and is configured by a random access memory (RAM). The CPU 21 loads the control program stored in the storage device 23 to the memory 22 and executes processes based on the program, to thereby generally control the respective units of the computer. The communication I/F 24 is a network interface that performs a transmission control with respect to the network 14.

Hereinafter, the CPU 21, the display 28, the storage device 23, and the like which are basic components of the computer shown in FIG. 4 are assigned a subscript sign "A" when being described as components of the client terminal 12, like a CPU 21A, and are assigned a subscript sign "B" when being described as components of the medical care support server 11, like a CPU 21B.

Figure 5:
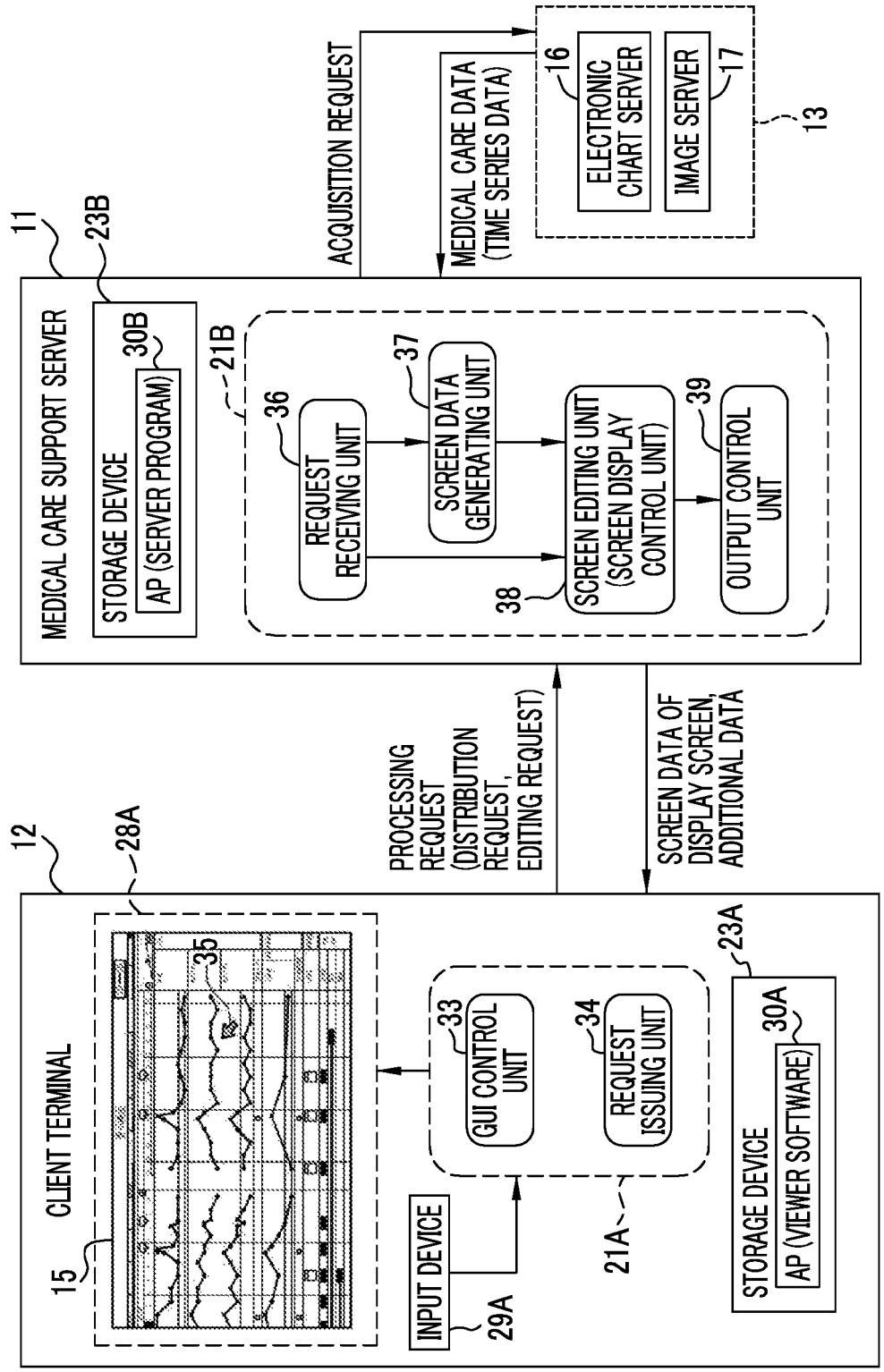
FIG. 5 is a diagram illustrating an overview of functions of a client terminal and a medical care support server.

As shown in FIG. 5, in a storage device 23A of the client terminal 12, a client program such as electronic chart software for viewing or editing of an electronic chart, or viewer software for viewing an examination image or a display screen 15 is installed as an AP 30A. The viewer software may be dedicated software, or may be a general-purpose WEB browser.

In the client terminal 12, if the viewer software is activated, for example, a startup screen including an operating function based on a graphical user interface (GUI) is displayed on a display 28A of the client terminal 12, and the CPU 21A of the client terminal 12 cooperates with the memory 22 or the like to function as a GUI control unit 33 and a request issuing unit 34 that issues various requests to the medical care support server 11. On the startup screen, an operation instruction such as designation of a patient ID or a distribution instruction of medical care data is performed.

The medical care support server 11 distributes screen data that fin Ins the display screen 15. The screen data may be configured by data described in a markup language such as an extensible markup language (XML), for example. The GUI control unit 33 reproduces the display screen 15 on the basis of the received screen data, and displays the display screen 15 on the display 28A. The display screen 15 also functions as an operating screen. The GUI control unit 33 controls the GUI according to an operation instruction input from an input device 29A through the display screen 15, such as a click operation of an operating button using a pointer 35 of a mouse.

The request issuing unit 34 issues a processing request with respect to the medical care support server 11. If designation of a patient ID and a distribution instruction of the display screen 15 are received through the GUI control unit 33, the request issuing unit 34 issues a distribution request of screen data of the display screen 15 as the processing request. The distribution request also includes a distribution request of additional data of medical care data. In a case where the medical care data is time series data obtained over a long period, there is a case where the data over the entire period cannot be delivered at once. In such a case, in response to designation of a display period on the display screen 15, a screen scroll operation for changing the display period, or the like, the request issuing unit 34 requests the medical care support server 11 to deliver undelivered additional data. Further, if an editing request of the display screen 15 is received through the GUI control unit 33, the request issuing unit 34 issues an editing request. The processing request such as an issued distribution request or editing request is transmitted to the medical care support server 11 through the network 14.

A server program for causing a computer to function as the medical care support server 11 is installed in a storage device 23B of the medical care support server 11, as an AP 30B. In this example, the server program functions as a time series data display control program of the invention. If the server program is executed, the CPU 21B of the medical care support server 11 cooperates with the memory 22 or the like to function as a request receiving unit 36, a screen data generating unit 37, a screen editing unit 38, and an output control unit 39.

The request receiving unit 36 receives a processing request from the client terminal 12. If a distribution request of medical care data, the request receiving unit 36 inputs a distribution command based on content of the distribution request to the screen data generating unit 37. The distribution request includes a designated patient ID, and the request receiving unit 36 inputs a command for generating screen data of the display screen 15 relating to medical care data of the designated patient ID to the screen data generating unit 37.

The screen data generating unit 37 issues an acquisition request of the medical care data of the designated patient ID to the server group 13, and acquires the medical care data. A temporal range of the acquired medical care data is an entire range of the medical care data that exists in the server group 13, for example. For example, in a case where one patient repeatedly receives an intermittent ambulatory care or repeatedly enters and leaves a hospital, medical care data intermittently exists. In this case, the entirety of the intermittent medical care data becomes an acquisition target. The screen data generating unit 37 generates screen data of the display screen 15 that displays the acquired medical care data as time series data.

The editing request input to the request receiving unit 36 is input to the screen editing unit 38. The screen editing unit 38 edits screen data of the display screen 15 on the basis of the editing request. The editing request includes a request for switching between a two-dimensional display mode and a three-dimensional display mode with respect to a display mode of the display screen 15 (which will be described later). The screen editing unit 38 functions as a screen display control unit for performing display mode switching on the basis of the display mode switching request. Further, the screen editing unit 38 performs an editing process with respect to the screen data generated by the screen data generating unit 37 as necessary.

The output control unit 39 performs a control for distributing the screen data of the display screen 15 generated by the screen data generating unit 37, additional data with an additional distribution instruction, edited screen data which is edited by the screen editing unit 38, or the like, to the client terminal 12 through the communication I/F 24.

Figure 6:
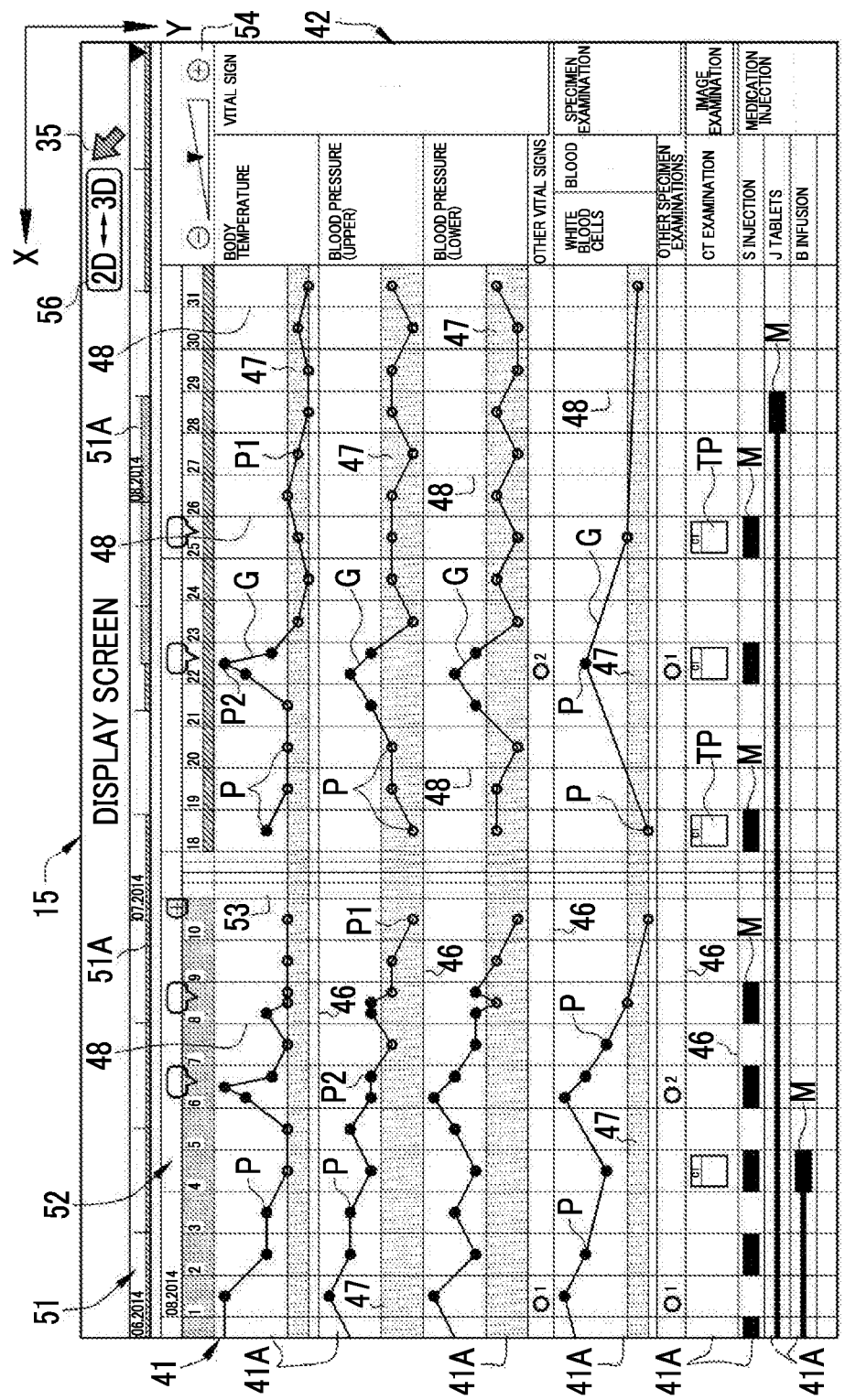
FIG. 6 is a diagram illustrating an example of a display screen in a two-dimensional display mode.

As shown in FIG. 6, the display screen 15 has a main display region 41 and an item name display region 42. In the display screen 15, the transverse axis (X axis) is set as a time axis, and the longitudinal axis (Y axis) is set as a data item array axis, respectively. On the time axis, the left direction represents a past time and the right direction represents a current time. The main display region 41 is a region where a plurality of pieces of medical care data (time series data) are displayed for each data item. The data items of this example include a body temperature, a blood pressure (upper), and a blood pressure (lower) as measurement values of vital signs, white blood cells in blood examination as an examination value of a specimen test, and examination images in CT examination as examination data in image examination.

The main display region 41 has a plurality of sub regions 41A defined for each data item, and medical care data for each data item is displayed in each sub region 41A. Each sub region 41A is a data display row in which a longitudinal direction extends in the time axis direction and a height indicating each piece of data is shown. The respective sub regions 41A are divided by lateral grid lines 46 extending in the direction of the transverse axis (X axis).

Further, an interval between the lateral grid lines 46 may be adjusted. By adjusting the interval between the lateral grid lines 46, it is possible to adjust the height (the width in the longitudinal axis direction) of each sub region 41A. For example, by designating the lateral grid line 46 using a pointer 35 and performing a drag operation of a mouse, it is possible to change the interval between the lateral grid lines 46. Thus, the height of each sub region 41A can be adjusted.

In each sub region 41A, display forms of medical care data (time series data) vary according to data items. For example, a body temperature, a blood pressure (upper), and a blood pressure (lower) which correspond to data items of vital signs, and white blood cells which corresponds to a data item of a specimen test are displayed in the form of a polygonal line graph G, respectively. The polygonal line graph G is a graph obtained by connecting input points P where medical care data exists by line segments.

For each examination image, a thumbnail image TP is displayed on an acquisition date of the examination image. The thumbnail image TP is an icon capable of being clicked by a mouse, for example, and an actual image corresponding to the thumbnail image TP is displayed by a click operation.

Further, for S injection liquid, J tablets, and B infusion which correspond to data items of medication and injection, a rectangular mark M is displayed at administered date and time. In the data items of medication and injection, in a case where the administered date and time are continuous like the J tablets and the B infusion, the display is performed in such a form that marks M are displayed on the first date and the last date of the continuously administered period, respectively, and the first date and the last date are connected by a line segment. The respective sub regions 41A are arranged in the longitudinal axis (Y axis), so that the longitudinal axis becomes the data item array axis on the display screen 15.

The height direction of each sub region 41A where the polygonal line graph G is displayed corresponds to a fluctuation direction of data values of the polygonal line graph G. In each sub region 41A, a reference numeral 47 indicated by dot hatching represents a normal range mark indicating a range set as a normal range of data values for each data item. For example, in the case of the body temperature, a range of 36° C. to 37° C. is set as a normal range, and the normal range mark 47 is displayed in the range. The respective normal marks 47 are also displayed with respect to the blood pressure (upper), the blood pressure (lower), and the white blood cells.

Further, in the polygonal line graph G, in a case where a data value is within the normal range, each input point P is displayed by an outline dot which is displayed only with a circular contour line and is not colored inside the contour line, as shown at an input point P1. Further, in a case where a data value is out of the normal range, each input point P is displayed by a solid dot which is colored inside the circular contour line, as shown at an input point P2. In this way, by providing the normal range mark 47, and by selectively using an outline dot and a solid dot as a display form of the input point P depending on whether data value is within the normal range, it is possible to easily recognize whether the data value is normal or not.

In addition, in the main display region 41, vertical grid lines 48 are provided in the longitudinal direction (Y axis) on a daily basis, and the width of a daily column may be specified by an interval between two contiguous vertical grid lines 48. Similar to the lateral grid lines 46, the interval between the vertical grid lines 48 can be adjusted. By adjusting the interval between the vertical grid lines 48, it is possible to increase or decrease the width of the daily column. A method for adjusting the interval between the vertical grid lines 48 may be performed by designating the vertical grid line 48 using the pointer 35 and performing a drag operation of a mouse, similar to the lateral grid line 46.

Further, the screen of the main display region 41 may be scrolled in the transverse direction (X axis direction) and the longitudinal direction (Y axis direction). Through a screen scroll operation in the transverse direction, a display range of medical care data such as the polygonal line graph G displayed in the main display region 41 may be changed. In a case where an ambulatory care period or a hospitalization period of a patient is long, or in a case where a patient repeatedly enters and leaves a hospital, a period during which medical care data exists lasts for a long time. Since the screen size of the display 28A is limited, the entire period of the long-term medical care data cannot be displayed in the main display region 41 at once. In the example shown in FIG. 6, in the entire period during which the medical care data exists, a display range of the main display region 41 corresponding to about one month of August 2014 is displayed. Through the screen scroll operation in the transverse direction, the display range of the main display region 41 may be changed from August 2014 to one month of July or June, for example.

Further, through a screen scroll operation in the longitudinal direction, data items which are not displayed may be displayed. For example, in the example shown in FIG. 6, as the data items of medication and injection, the data items of the S injection, the J tablets, and the B infusion are displayed, but in a case where there is data of additional another medicine that is not displayed, it is possible to display the medicine through the screen scroll operation in the longitudinal direction.

In addition, as described later, the main display region 41 may be displayed in two display modes of a two-dimensional (2D) display mode in which medical care data (time series data) is displayed on a two-dimensional plane formed by two axes of the time axis (transverse axis) and the data array axis (longitudinal axis), as shown in FIG. 6, and a three-dimensional (3D) display mode (see FIGS. 7 and 8) in which the two-dimensional plane on which the medical care data is displayed is three-dimensionally displayed using the laws of perspective.

The item name display region 42 is disposed at the right end of the main display region 41. An item name of medical care data displayed in each sub region 41A is displayed in the item name display region 42. In the item name display region 42, category names to which each data name belongs, such as vital, specimen examination, image examination, medication, or injection, are also displayed, in addition to item names such as a body temperature, a blood pressure (upper), a blood pressure (lower), white blood cells, CT examination, or S injection.

Two time axes of a first time axis 51 and a second time axis 52 are provided on the display screen 15. The first time axis 51 is provided above the main display region 41, and the second time axis 52 is provided at an upper end in the main display region 41. The second time axis 52 is a time axis indicating a display period in the main display region 41. The second time axis 52 has a width in the longitudinal direction, in which numerals indicating a year, a month and a date, and a scale set per day are displayed. In FIG. 6, in the main display region 41, medical care data corresponding to one month of August 2014 is displayed, and correspondingly, medical care data corresponding to about one month of August 2014 is displayed on the second time axis 52.

On the other hand, on the first time axis 51, a relatively long display period may be displayed, compared with the second time axis 52. In the two-dimensional display mode, the first time axis 51 is set to a relatively long display period, compared with the second time axis 52. In the example of FIG. 6, a display period of the second time axis 52 is set to about one month of August 2014, whereas a display period of the first time axis 51 is set to about three months from June 2014 to August 2014. Similar to the second time axis 52, the first time axis 51 has a width in the height direction, in which numerals indicating a year and a month, and a scale for dividing a period at a predetermined interval are displayed.

On the first time axis 51, an existence mark 51A indicating a period during which medical care data exists may be displayed. Through the existence mark 51A, it is possible to check the period during which the medical care data exists in the display period of the first time axis 51. Further, on the first time axis 51, if an arbitrary time is designated using the pointer 35, medical care data at the arbitrary time can be displayed in the main display region 41. For example, on the first time axis 51, if the existence mark 51A of June 2014 is designated using the pointer 35, the display period displayed in the main display region 41 is changed from August 2014 to June 2014.

Further, in the main display region 41, a reference numeral 53 represents a compression mark indicating a compression period. In the case of a patient who is not hospitalized but is receiving medical treatment as an outpatient, or in the case of a patient who repeatedly enters and leaves a hospital, a blank period during which there is no medical care data occurs. In the blank period during which there is no medical care data, only a blank is displayed in the main display region 41, so that the display space is merely wasted. Thus, in the main display region 41, with respect to the blank period during which there is no medical care data, the display period is compressed in the time axis direction, and the compressed mark 53 is displayed therefor. The compressed mark 53 is displayed in such a form that the interval between the vertical grid lines 48 is narrowed to become compact, for example. In this example, since a period from Aug. 11, 2014 to August 17 is a blank period of medical care data, the compressed mark 53 is displayed for the blank period. Thus, it is possible to effectively use the limited main display region 41.

In addition, a display magnification change unit 54 for changing a magnification for displaying the main display region 41 is provided on the right side of the second time axis 52 and above the item name display region 42. The display magnification change unit 54 enlarges or reduces a display magnification of the entire main display region 41 by a slide operation of a slider in a plus direction (enlarging direction) or a minus direction (reduction direction).

By enlarging the display magnification, it is possible to display the polygonal line graph G or the thumbnail image TP in the main display region 41 in an enlarged size. Contrarily, in the transverse direction, the display period is shortened, and the number of data items displayed in the longitudinal direction decreases. On the other hand, if the display magnification is reduced, the polygonal line graph G or the thumbnail image TP in the main display region 41 is displayed in a reduced size, but contrarily, the display period is lengthened, and the number of data items to be displayed increases.

Further, a display mode switching button 56 is provided above the first time axis 51. The display mode switching button 56 is an operation unit for inputting an operation instruction of switching of the display mode of the main display region 41 between the two-dimensional display mode and the three-dimensional display mode, and is operated by a click operation of a mouse through the pointer 35.

In the two-dimensional display mode, as shown in FIG. 6, the main display region 41 is displayed on the two-dimensional plane formed by two axes of the time axis (transverse axis) and the data array axis (longitudinal axis). In the two-dimensional display mode, medical care data (time series data) is displayed on this two-dimensional plane. In this state, if the display mode switching button 56 is operated, the display mode of the main display region 41 is switched into the three-dimensional display mode shown in FIG. 7.

Figure 7:
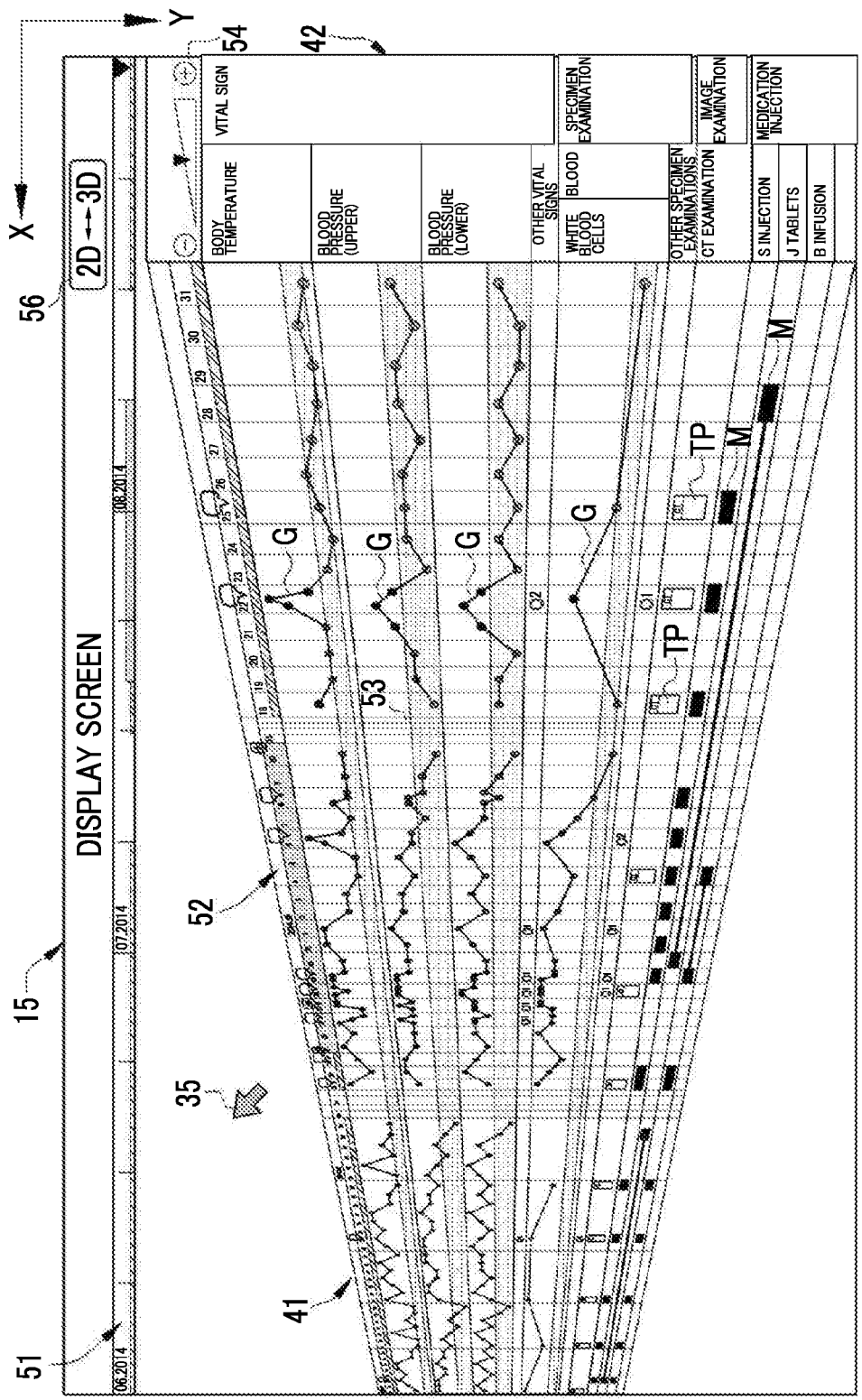
FIG. 7 is a diagram illustrating an example of a display screen in a three-dimensional display mode.

As shown in FIG. 7, the three-dimensional display mode is a display mode in which a two-dimensional plane on which medical care data (time series data) is displayed is three-dimensionally displayed, using the laws of perspective by which a plurality of straight lines parallel to the time axis in the two-dimensional display mode are drawn to be converged toward the past on the time axis. In this example, the three-dimensional display mode is a display mode in which the two-dimensional plane in the two-dimensional display mode is virtually rotated around a rotation axis, using the longitudinal axis (Y axis) orthogonal to the time axis (X axis) as the rotation axis. Such a virtual three-dimensional process may be performed using an image processing technique for setting a virtual three-dimensional space and allocating data on a two-dimensional plane in the set three-dimensional space, for example.

Further, in the three-dimensional display mode, a time scale of the main display region 41 is set so that the time scale becomes long with respect to the two-dimensional display mode. Thus, compared with the two-dimensional display mode, in the three-dimensional display mode, a display period of medical care data becomes long. In this example, the display period of the main display region 41 is about one month of August 2014 in the two-dimensional display mode shown in FIG. 6, but is about three months from June 2014 to August 2014 in the three-dimensional display mode shown in FIG. 7.

With such a three-dimensional display, as the time goes farther to the past, the display magnification is more reduced, and the display size becomes smaller, but compared with a case where the past time and the current time are switched by a screen scroll operation in the two-dimensional display for display, it is possible to easily recognize a long-term tendency of medical care data at a glance.

Particularly, by combining the laws of perspective and the prolonged time scale, it is possible to recognize an entire tendency over a long period due to a synergistic effect with the laws of perspective. Thus, using the two-dimensional display mode in recognition of short-term changes in time series data and details thereof, and using the three-dimensional display mode in recognition of an entire tendency over a long period, it is possible to check short-term and long-term time series data using a simple operation while reducing a screen scroll operation.

Further, by setting a transverse axis of the display screen 15 as a time axis and a longitudinal axis thereof as a data array axis in the two-dimensional display mode, and by setting the data array axis orthogonal to the time axis as a rotation axis in the three-dimensional display mode, a virtual rotation of the main display region 41 is performed. Since the time axes in the two-dimensional display mode and the three-dimensional display mode coincide with each other in the transverse axis direction, even if switching between the two-dimensional display and the three-dimensional display is performed, it is possible to easily recognize the displays with little discomfort.

In addition, a time scale of a second time axis 52 in the main display region 41 is naturally changed according to the change in the time scale of the main display region 41. In addition to the second time axis 52, a time scale of the first time axis 51 is also changed in conjunction with switching of the display mode. In this example, in the three-dimensional display mode, the time scale of the first time axis 51 is changed so that the time scale of the first time axis 51 and the time scale of the main display region 41 coincide with each other. Thus, the same display period as the display period of the main display region 41, corresponding to about three months from June 2014 to August 2014, is displayed on the first time axis 51.

Figure 8:
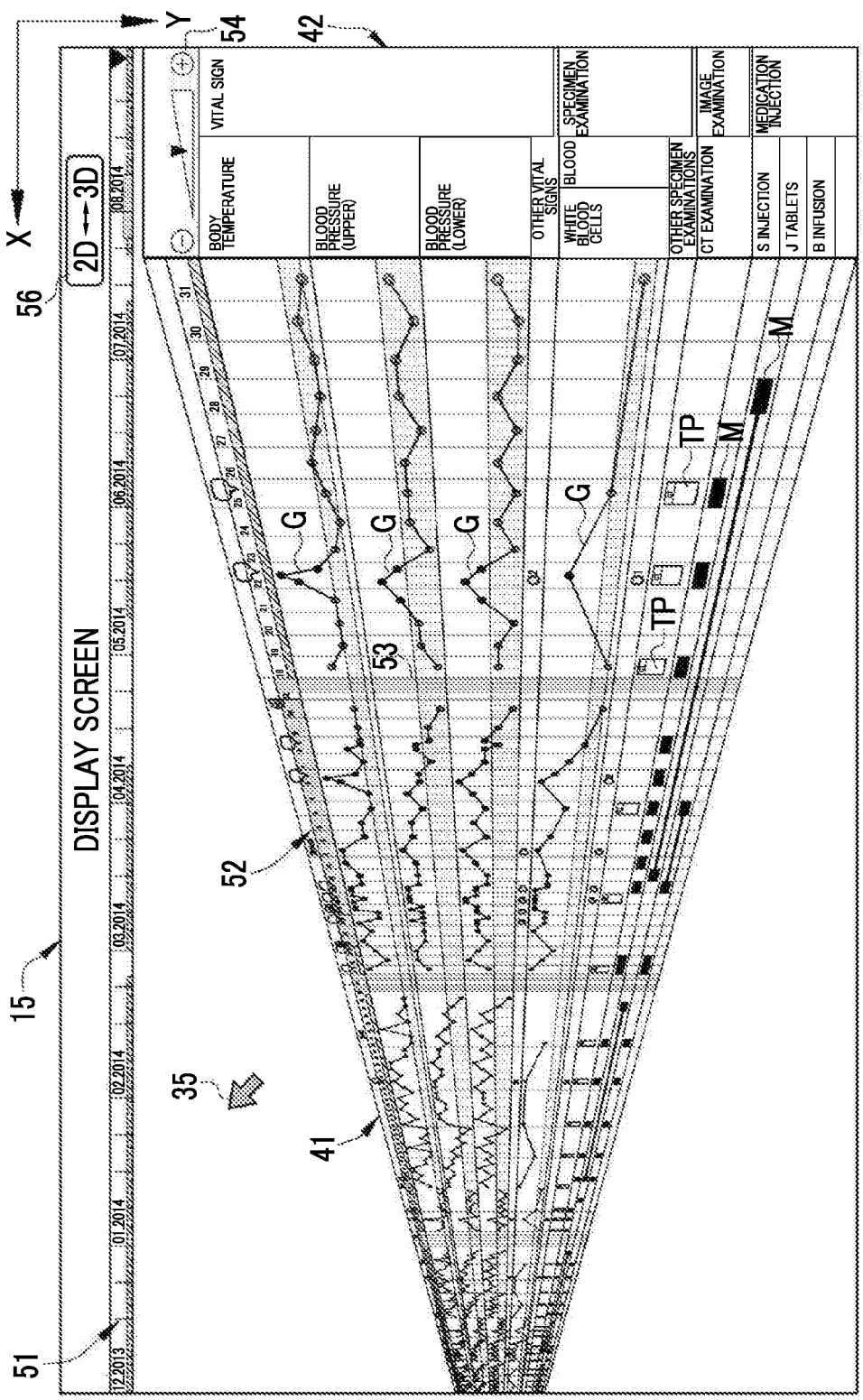
FIG. 8 is a diagram illustrating another example of the display screen in the three-dimensional display mode.

Further, as shown in FIG. 8, in the three-dimensional display mode, the virtual rotation angle of the main display region 41 may be changed. In the example shown in FIG. 8, the rotation angle of the main display region 41 is larger than that in the example shown in FIG. 7.

Figure 9:
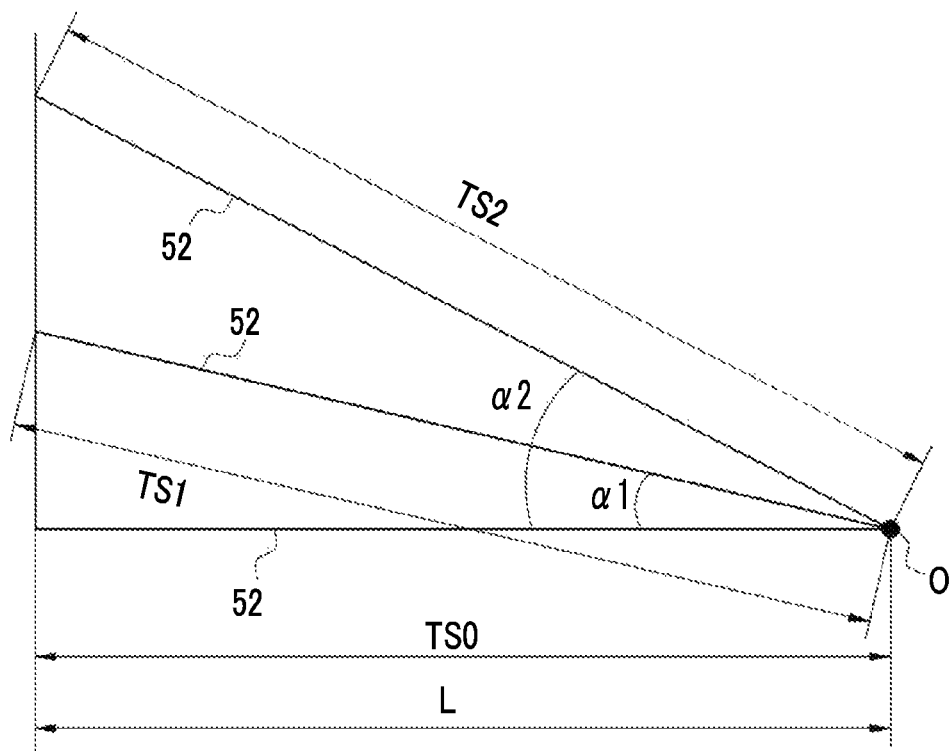
FIG. 9 is a diagram illustrating a virtual rotation angle.

FIG. 9 conceptually shows the virtual rotation in the three-dimensional display mode. In FIG. 9, reference sign L represents a lateral width in which the main display region 41 is displayed in the two-dimensional display mode, on the screen of the display 28A. In the two-dimensional display mode, the lateral width L of the display 28A is parallel to the second time axis 52.

Reference sign O represents a rotation axis (Y axis) orthogonal to the time axis in the two-dimensional display mode. In the three-dimensional display mode, the main display region 41 is virtually rotated around the rotation axis O. If the time scale of the second time axis 52 in the two-dimensional display mode is set as TS0, the time scale of the second time axis 52 in the main display region 41 becomes TS1 (>TS0) in a case where the rotation angle is α1. Further, if the rotation angle is increased from α1 to α2, the time scale of the second time axis 52 is set to become TS2 (>TS1) from TS1.

Figure 10:
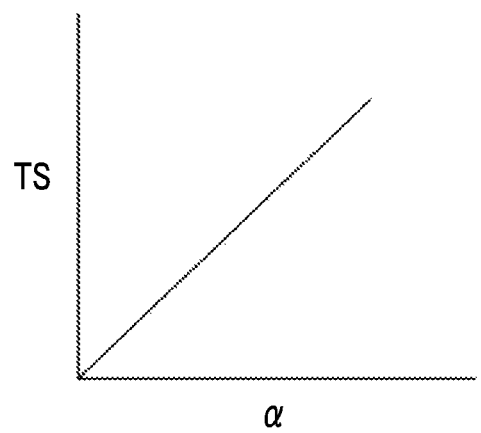
FIG. 10 is a graph illustrating a relationship between a rotation angle and a time scale.

That is, in FIG. 10, as shown in the relationship between the rotation angle α and the time scale TS of the second time axis 52, the time scale TS of the second time axis 52 is set to become larger according to the size of the rotation angle α.

In this way, by setting the time scale TS of the second time axis 52 to become larger according to the size of the rotation angle α, it is possible to display longer-term medical care data, and to easily check change in medical care data over a long period in the past. In addition, unlike a screen scroll for switching between display periods, according to the three-dimensional display of this example, it is possible to view an overall tendency of long-term medical care data.

Further, the first time axis 51 is two-dimensionally displayed even in the three-dimensional display mode, similar to the two-dimensional display mode. On the other hand, the second time axis 52 is three-dimensionally displayed, similar to the main display region 41. As described above, the display period of the first time axis 51 is changed in conjunction with the display period of the second time axis 52. In this way, even in a case where the main display region 41 is three-dimensionally displayed, since the first time axis 51 is two-dimensionally displayed, it is possible to easily check a display period of the main display region 41 or a time of medical care data.

In addition, the item name display region 42 is two-dimensionally displayed even in the three-dimensional display mode, unlike the main display region 41. Thus, it is possible to easily check item names. Further, the item name display region 42 is disposed at a right end of the main display region 41 on the display screen 15, that is, at an end in a current direction on the time axis. In the three-dimensional display mode, the main display region 41 has a large display magnification toward the current direction. Accordingly, by disposing the item name display region 42 at the end in the current direction, it is possible to set a display magnification of the item name display region 42 to be large, and thus, it is possible to easily check the item names.

Hereinafter, operations according to the configuration will be described with reference to a flowchart shown in FIG. 11. A doctor who treats a patient views medical care data through the client terminal 12. The doctor starts up viewer software of the client terminal 12, designates a patient ID, and inputs a distribution instruction of medical care data (S (step) 1010).

Thus, a distribution request issued from the request issuing unit 34 of the client terminal 12 is transmitted to the medical care support server 11. The medical care support server 11 inputs, if the request receiving unit 36 receives the distribution request, the distribution request to the screen data generating unit 37. The screen data generating unit 37 transmits an acquisition request of medical care data of the designated patient ID to the server group 13, and acquires the medical care data (S2010).

In the medical care support server 11, the screen data generating unit 37 generates screen data of the display screen 15 on the basis of the acquired medical care data (S2020). The screen editing unit 38 edits the screen data as necessary, and inputs the screen data to the output control unit 39. The output control unit 39 distributes the screen data to the client terminal 12 which is a request source through the communication OF 24 (S2030).

If the screen data is received, the client terminal 12 reproduces the display screen 15 shown in FIG. 6, for example, on the basis of the screen data received by the GUI control unit 33, and displays the result on the display 28A (S1020). In the display screen 15 shown in FIG. 6, since the main display region 41 is displayed in the two-dimensional display mode, in a case where the doctor wants to display the main display region 41 in the three-dimensional display mode. In this case, as shown in FIGS. 7 and 8, the doctor operates the display mode switching button 56.

If the display mode switching operation (screen editing operation) is made (Y in S1030), the request issuing unit 34 issues an editing request on the basis of a screen editing request (S1040). The editing request is transmitted to the medical care support server 11. In the medical care support server 11, if the editing request is received, the request receiving unit 36 inputs the editing request to the screen editing unit 38. The screen editing unit 38 performs a screen display control for switching the screen data of the display screen 15 from the two-dimensional display mode into the three-dimensional display mode by a screen editing process (S2040). The screen data after editing is distributed to the client terminal 12 which is the request source by the output control unit 39 (S2050).

If the screen data after editing is received, the client terminal 12 reproduces and displays the display screen 15 on the basis of the screen data after editing (S1050). Thus, the doctor can view the main display region 41 in the three-dimensional display mode. In the three-dimensional display mode, a time scale of the main display region 41 is longer than that in the two-dimensional display mode, and thus, it is possible to view medical care data over a long period.

With respect to the medical care data, in many cases, a medical care of a patient is performed over a long period, or a medical care is intermittently performed while a patient repeatedly enters and leaves a hospital. In such a case, an acquisition period of medical care data becomes long. It is natural that long-term medical care data has a long time axis. The medical care data is used by a doctor for use in determining a medical care policy of a patient. In determination of the medical care policy, it is important to recognize both of the presence or absence of a short-term change of time series data relating to a medical care or details thereof and an overall tendency over a long period.

According to this embodiment, it is possible to view medical care data in both the two-dimensional display mode and the three-dimensional display mode with a time scale longer than that in the two-dimensional display mode. In the two-dimensional display mode, since medical care data is displayed by a two-dimensional plane, the presence or absence of change in data values for a short period and details thereof are easily checked. On the other hand, in the three-dimensional display mode with a long time scale, while it is difficult to check a detailed change in data values, it is possible to suitably recognize an overall tendency over a long period. The switching between two display modes of the two-dimensional display mode and the three-dimensional display mode can be easily performed by an operation of the display mode switching button 56, for example. Thus, a doctor can easily recognize both of the presence or absence of a short-term change of medical care data of a patient and details thereof and an overall tendency over a long period, using both the two display modes.

Figure 11:
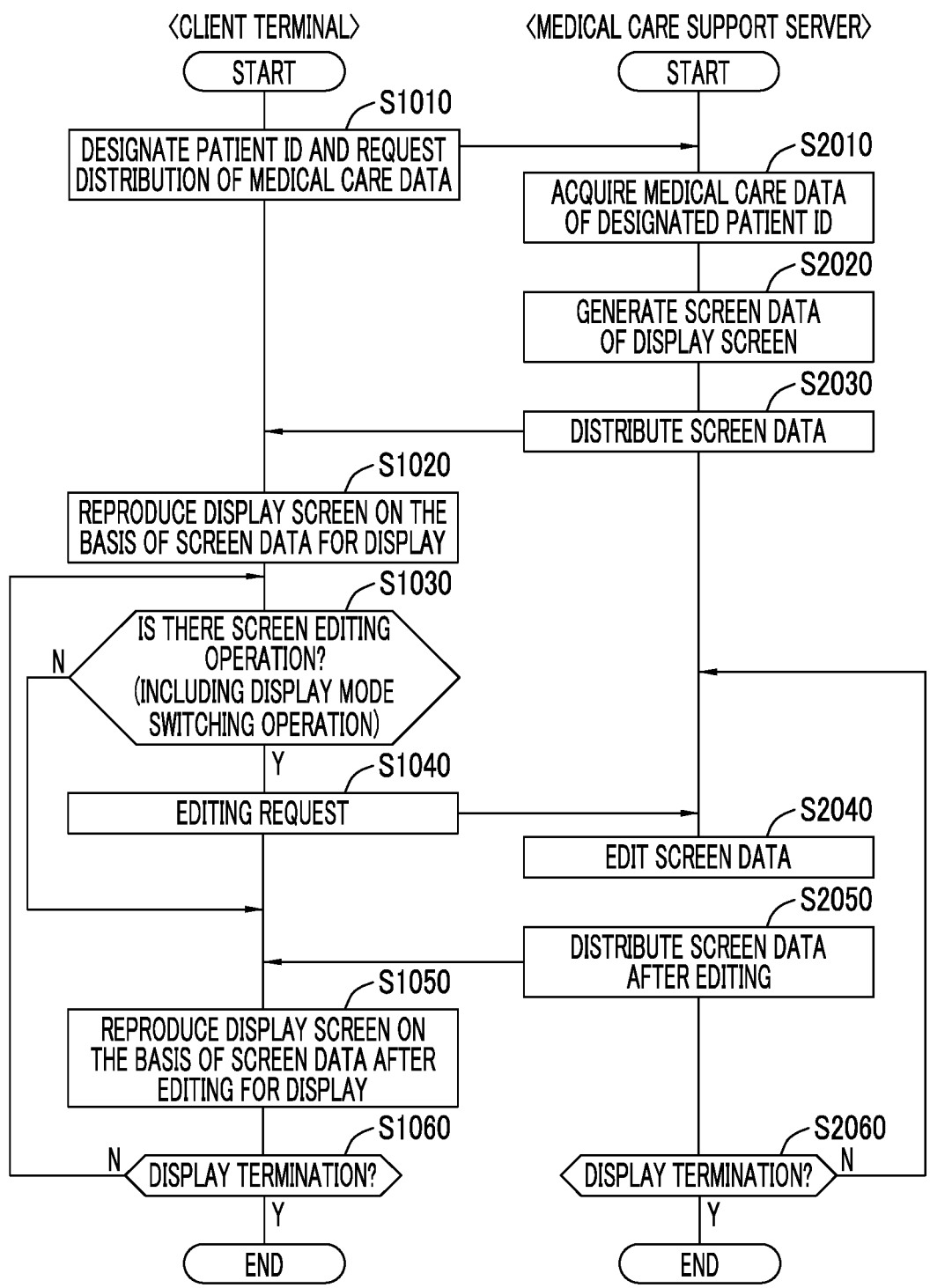
FIG. 11 is a flowchart illustrating a processing procedure.

In FIG. 11, the client terminal 12 repeats the above-described steps until there is a display termination instruction (Y in S1060). For example, in a case where an operation for returning to the two-dimensional display mode from the three-dimensional display mode or another editing operation such as an additional data request is performed, the client terminal 12 transmits a distribution request or an editing request based on such an operation to the medical care support server 11. In the medical care support server 11, in a case where there is the additional data distribution request or another editing request from the client terminal 12, the screen editing unit 38 performs an editing process, and distributes screen data after editing. The medical care support server 11 repeats the editing process until there is a display termination instruction in the client terminal 12 (Y in S1060 and Y in S2060).

The three-dimensional display mode of this example is a display mode in which the two-dimensional plane in the two-dimensional display mode is virtually rotated around a rotation axis using the longitudinal axis (Y axis) orthogonal to the time axis (X axis) as the rotation axis. Thus, compared with the three-dimensional display using the circumferential surface of the virtual cylinder disclosed in JP1994-243264A (JP-H6-243264A), the data array axis is not curved, and thus, time series data is easily viewed. Particularly, since a fluctuation direction of data values of the time series data and the data array axis coincide with each other, fluctuation of the data values is also easily recognized. Further, even in the three-dimensional display mode, since the first time axis 51 and the item name display region 42 are two-dimensionally displayed, a time of medical care data and item names thereof are easily checked.

Further, in the three-dimensional display mode of this example, a form in which the main display region 41 is virtually rotated using the longitudinal axis (Y axis) of the display 28A as a rotation axis is described, but a form in which the main display region 41 is virtually rotated using the transverse axis (X axis) of the display 28A as a rotation axis may be used. In this case, for example, the data array axis is set along the transverse axis (X axis), and the item name display region 42 is disposed in a lower part of the display screen 15. Further, the time axis of the main display region 41 is set so that a downward direction on the display screen 15 is a current direction and an upward direction thereon is a past direction. In this form, the main display region 41 shown in FIGS. 7 and 8 has a display form in which it is rotated as if at an angle of 90 degrees.

[Second Embodiment]

Figure 12:
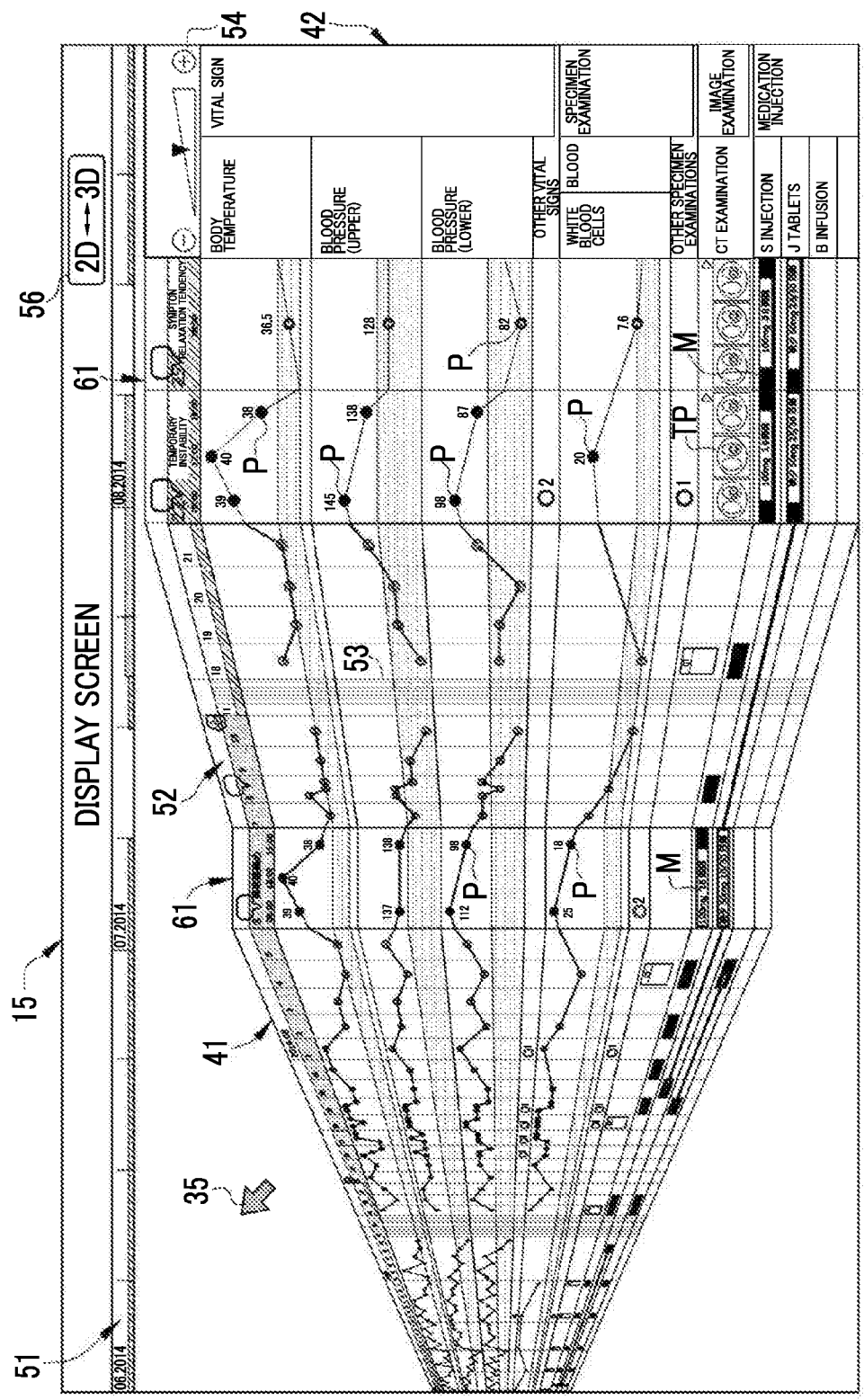
FIG. 12 is a diagram illustrating a display screen in a three-dimensional display mode according to a second embodiment.
Figure 13:
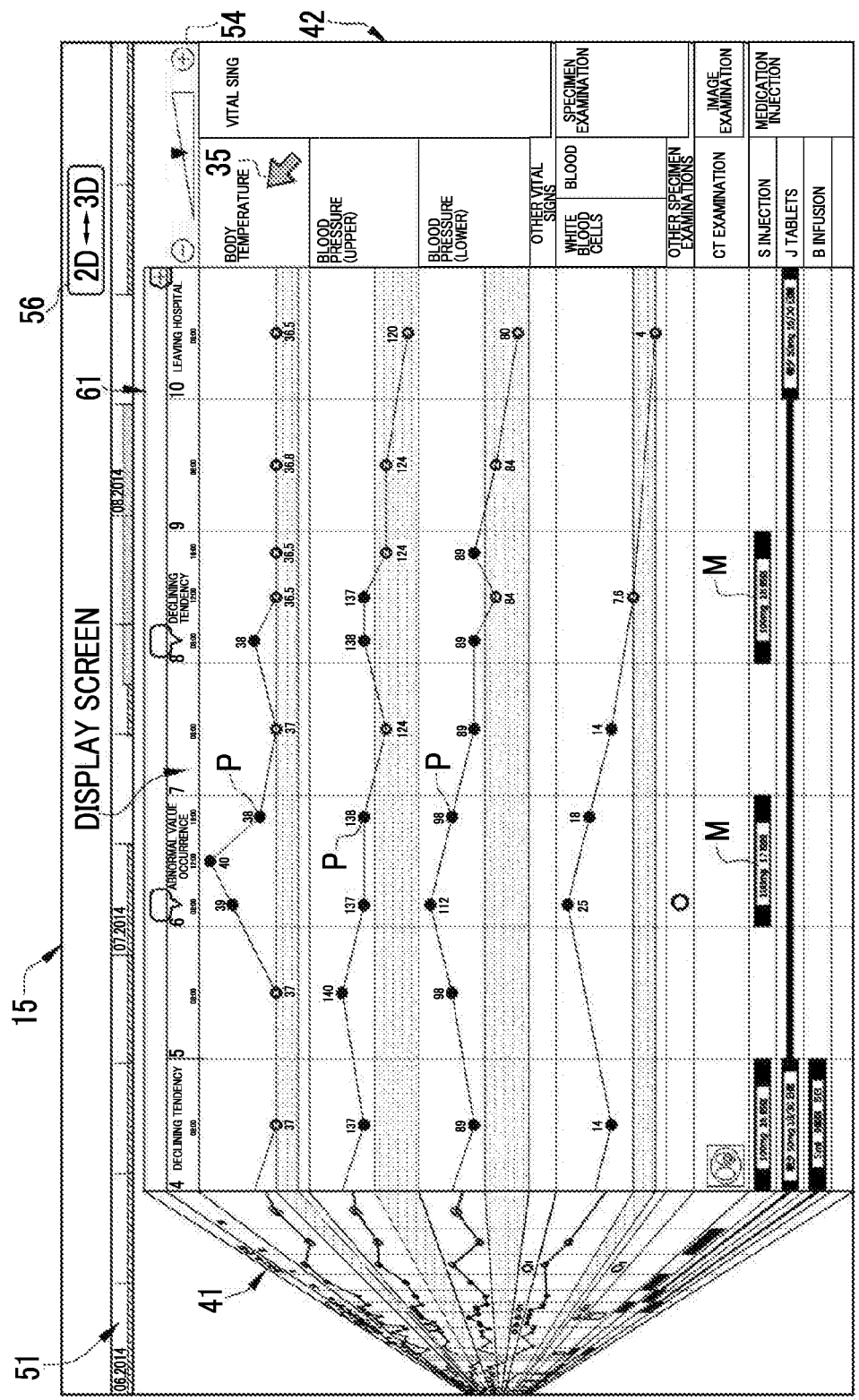
FIG. 13 is a diagram illustrating another example of the display screen in the three-dimensional display mode according to the second embodiment.

As in a second embodiment shown in FIGS. 12 and 13, in the three-dimensional display mode, a part of the main display region 41 may be two-dimensionally displayed. In FIG. 12, the main display region 41 is displayed in the three-dimensional display mode. A two-dimensional display region 61 is provided at a part of the main display region 41.

In an example of FIG. 12, a display period of the main display region 41 corresponds to about three months from June 2014 to August 2014. Here, three days of 6, 22 and 23 August, 2014 correspond to the two-dimensional display region 61. In an example of FIG. 13, seven days from 4 to 10 August among about three months from June 2014 to August 2014 correspond to the two-dimensional display region 61.

The two-dimensional display region 61 is suitable for checking change in data or details thereof, compared with the three-dimensional display. In the two-dimensional display region 61, detailed display can be performed, compared with the three-dimensional display. Thus, even in the three-dimensional display mode, by partially allowing the two-dimensional display, it is possible to easily check details of medical care data at an arbitrary time.

In addition, with respect to detailed display of the two-dimensional display region 61, specifically, specific numerical values of data are displayed in the vicinity of input points P of the polygonal line graph G, and comments input in the vicinity of date display (in the example of FIG. 12, primary instability, and symptom relaxation tendency, and in the example of FIG. 13, abnormal value occurrence, declining tendency, and the like) are displayed. Further, the display content of the thumbnail image TP is displayed in detail, the dose, the number of times of administration, and the like are also displayed with respect to the marks M for medication and injection.

A switching operation between the three-dimensional display and the two-dimensional display region 61 is performed by designating a desired date using the pointer 35 of the mouse in the main display region 41, and performing a click operation, for example. If the click operation is performed again, the original state is restored.

[Third Embodiment]

In the above-described respective embodiments, an example in which the time series data display control device of the invention is provided in the form of the medical care support server 11 that distributes screen data of the display screen 15 on the basis of a request of the client terminal 12 is shown, but as shown in FIG. 14, a configuration in which the client terminal 12 functions as a time series data display control device may be used. In FIG. 14, the same reference numerals are given to the same portions as in the above-described embodiments, and description thereof will not be repeated.

The third embodiment is different from the first embodiment in that the CPU 21A executes the viewer software of the client terminal 12 to function as the screen data generating unit 37 and the screen editing unit 38.

In the client terminal 12, the screen data generating unit 37 directly accesses the server group 13 to obtain medical care data and to generate screen data of the display screen 15. The GUI control unit 33 reproduces the display screen 15 on the basis of the generated screen data, and displays the result on the display 28A. The screen editing unit 38 performs a screen display control for switching between the two-dimensional display mode and the three-dimensional display mode with respect to a display mode of the display screen 15 on the basis of a display mode switching instruction. In the third embodiment, the viewer software functions as a time series data display control program.

In this way, the time series data display control device is not limited to the form of the medical care support server 11 that distributes screen data as in the first embodiment, and may have the form of the client terminal 12 as in the third embodiment.

Further, for example, as in a form in which generation of screen data is performed in the medical care support server 11 and the screen display control function for switching between the two-dimensional display mode and the three-dimensional display mode is performed in the client terminal 12, a part of the screen data generation function and the screen display control function may be performed on the medical care support server 11, and the other part thereof may be performed on a part of the client terminal 12. In this case, a computer system configured in the client terminal 12 and the medical care support server 11 functions as a time series data display control system.

As described above, the time series data display control device and system of the invention may be realized by various forms. Further, a hardware configuration of a computer system such as the medical care support server 11, the client terminal 12 may have various modifications. For example, the medical care support server 11 may be configured by a plurality of server computers separated as hardware for the purpose of improving its processing capacity and reliability. In this way, the hardware configuration of the computer system may be appropriately modified according to required performance such as a processing capacity, safety, or reliability. Further, the modification is not limited to the hardware configuration, and the time series data display control program may be duplicated, or may be dividedly stored in a plurality of storage devices in order to secure safety or reliability.

In addition, in the above-described respective embodiments, a form in which the medical care support server 11 and the client terminals 12 are used in one medical care facility is described, but for example, a form in which one medical care support server 11 is provided in an external data center and an application service such as a data distribution service of the medical care support server 11 in the data center can be used in the client terminals 12 in a plurality of medical care facilities may be used.

In this case, the medical care support server 11 is connected to the client terminals 12 provided in the plurality of medical care facilities to be communicable therewith through a wide area network (WAN) such as the Internet or a public communication network, for example. Further, the medical care support server 11 receives a request from each of the client terminals 12 in the plurality of medical care facilities, and provides an application service such as distribution of screen data of the display screen 15 to each client terminal.

For example, an installation location or an operation entity of the data center and the medical care support server 11 may be, for example, one of a plurality of medical care facilities, or may be a service company other than the medical care facilities. Further, in a case where a WAN such as a network is used, it is preferable to construct a virtual private network (VPN), or to use a communication protocol with a high security level such as Hypertext Transfer Protocol Secure (HTTPS) in consideration of information security.

Further, in the above-described respective embodiments, an example in which medical care data is used as time series data is shown, but the invention may be applied to time series data other than the medical care data. Even in the time series data other than the medical care data, in a case where it is necessary to repeatedly and alternately view a long-term tendency and a detailed short-term change, by applying the invention, it is possible to achieve superior effects. With respect to medical care data, since such a necessity for repeatedly and alternately recognizing and viewing a long-term tendency and a detailed short-term change is high as described above, application of the invention to medical care data is particularly useful.

The invention is not limited to the above-described embodiments, and may have various configurations without departing from the concept of the invention. For example, appropriate combinations of the above-described various embodiments or various modified examples may be used. Further, the invention is applied, in addition to a program, to a storage medium that stores the program.

EXPLANATION OF REFERENCES

11: medical care support server
12: client terminal
15: display screen
37: screen data generating unit
38: screen editing unit (screen display control unit)
39: output control unit
41: main display region
42: item name display region
51: first time axis
52: second time axis
56: display mode switching button

What is claimed is:

1. A time series data display control device comprising:
a processor configured to execute:
    a screen data generating unit that generates a time series data display screen on which a plurality of pieces of time series data are displayed; and
    a screen display control unit that performs switching between display modes of the time series data display screen, in which the display modes include two display modes of a two-dimensional display mode in which the time series data is displayed on a two-dimensional plane formed by two axes of a time axis of the plurality of pieces of time series data and a data array axis orthogonal to the time axis, on which the plurality of pieces of time series data are arrayed, and a three-dimensional display mode in which a time scale is set to be longer than a time axis of the two-dimensional display mode and the two-dimensional plane is three-dimensionally displayed using the laws of perspective by which a plurality of straight lines parallel to the time axis in the two-dimensional display mode are drawn to be converged toward the past on the time axis,
    wherein the three-dimensional display mode is a display mode in which the two-dimensional plane in the two-dimensional display mode is virtually rotated around a rotation axis orthogonal to the time axis, and
    wherein in the three-dimensional display mode, a part of a display period of the time series data is able to be two-dimensionally displayed,
wherein a rotation angle of the two-dimensional plane is changeable,
wherein the time scale of the time axis becomes longer as the rotation angle becomes larger,
wherein in the two-dimensional display mode, a transverse axis of the time series data display screen is set as the time axis, and a longitudinal axis thereof is set as the data array axis,
wherein in the three-dimensional display mode, the rotation axis and the longitudinal axis coincides with each other,
wherein the time series data display screen includes two time axes of a first time axis which is two-dimensionally displayed similar to the two-dimensional display mode even in the three-dimensional display mode, and a second time axis which is provided in the two-dimensional plane on which the time series data is displayed and is three-dimensionally displayed similar to the two-dimensional plane, and
wherein a display period of the first time axis is changed in conjunction with a display period of the second time axis which is changed depending on the rotation angle of the two-dimensional plane.

2. The time series data display control device according to claim 1,
wherein in the three-dimensional display mode, an item name display region for displaying respective item names of the plurality of pieces of time series data is two-dimensionally displayed.

3. The time series data display control device according to claim 2,
wherein on the time series data display screen, the item name display region is disposed at an end in a current direction on the time axis.

4. The time series data display control device according to claim 1,
wherein in the three-dimensional display mode, an item name display region for displaying respective item names of the plurality of pieces of time series data is two-dimensionally displayed.

5. The time series data display control device according to claim 4,
wherein on the time series data display screen, the item name display region is disposed at an end in a current direction on the time axis.

6. The time series data display control device according to claim 1,
wherein in the three-dimensional display mode, an item name display region for displaying respective item names of the plurality of pieces of time series data is two-dimensionally displayed.

7. The time series data display control device according to claim 6,
wherein on the time series data display screen, the item name display region is disposed at an end in a current direction on the time axis.

8. The time series data display control device according to claim 1,
wherein in the three-dimensional display mode, an item name display region for displaying respective item names of the plurality of pieces of time series data is two-dimensionally displayed.

9. The time series data display control device according to claim 1,
wherein in the three-dimensional display mode, an item name display region for displaying respective item names of the plurality of pieces of time series data is two-dimensionally displayed.

10. The time series data display control device according to claim 1,
wherein on the time series data display screen, a period during which the time series data does not exist is compressed in the time axis direction to be displayed.

11. The time series data display control device according to claim 1,
wherein on the time series data display screen, a period during which the time series data does not exist is compressed in the time axis direction to be displayed.

12. The time series data display control device according to claim 1,
wherein on the time series data display screen, a period during which the time series data does not exist is compressed in the time axis direction to be displayed.

13. The time series data display control device according to claim 1,
wherein the time series data is medical care data relating to a medical care of a patient.

14. A method for operating a time series data display control device, comprising:
a screen data generating step of generating a time series data display screen on which a plurality of pieces of time series data are displayed; and
a screen display control step of performing switching between display modes of the time series data display screen, in which the display modes include two display modes of a two-dimensional display mode in which the time series data is displayed on a two-dimensional plane formed by two axes of a time axis of the plurality of pieces of time series data and a data array axis orthogonal to the time axis, on which the plurality of pieces of time series data are arrayed, and a three-dimensional display mode in which a time scale is set to be longer than a time axis of the two-dimensional display mode and the two-dimensional plane is three-dimensionally displayed using the laws of perspective by which a plurality of straight lines parallel to the time axis in the two-dimensional display mode are drawn to be converged toward the past on the time axis,
wherein the three-dimensional display mode is a display mode in which the two-dimensional plane in the two-dimensional display mode is virtually rotated around a rotation axis orthogonal to the time axis, and
wherein in the three-dimensional display mode, a part of a display period of the time series data is able to be two-dimensionally displayed,
wherein a rotation angle of the two-dimensional plane is changeable,
wherein the time scale of the time axis becomes longer as the rotation angle becomes larger,
wherein in the two-dimensional display mode, a transverse axis of the time series data display screen is set as the time axis, and a longitudinal axis thereof is set as the data array axis,
wherein in the three-dimensional display mode, the rotation axis and the longitudinal axis coincides with each other,
wherein the time series data display screen includes two time axes of a first time axis which is two-dimensionally displayed similar to the two-dimensional display mode even in the three-dimensional display mode, and a second time axis which is provided in the two-dimensional plane on which the time series data is displayed and is three-dimensionally displayed similar to the two-dimensional plane, and
wherein a display period of the first time axis is changed in conjunction with a display period of the second time axis which is changed depending on the rotation angle of the two-dimensional plane.

15. A non-transitory computer readable recording medium storing a time series data display control program that causes a computer to function as a time series data display control device, comprising:
a screen data generating step of generating a time series data display screen on which a plurality of pieces of time series data are displayed; and
a screen display control step of performing switching between display modes of the time series data display screen, in which the display modes include two display modes of a two-dimensional display mode in which the time series data is displayed on a two-dimensional plane formed by two axes of a time axis of the plurality of pieces of time series data and a data array axis orthogonal to the time axis, on which the plurality of pieces of time series data are arrayed, and a three-dimensional display mode in which a time scale is set to be longer than a time axis of the two-dimensional display mode and the two-dimensional plane is three-dimensionally displayed using the laws of perspective by which a plurality of straight lines parallel to the time axis in the two-dimensional display mode are drawn to be converged toward the past on the time axis,
wherein the three-dimensional display mode is a display mode in which the two-dimensional plane in the two-dimensional display mode is virtually rotated around a rotation axis orthogonal to the time axis, and
wherein in the three-dimensional display mode, a part of a display period of the time series data is able to be two-dimensionally displayed,
wherein a rotation angle of the two-dimensional plane is changeable,
wherein the time scale of the time axis becomes longer as the rotation angle becomes larger,
wherein in the two-dimensional display mode, a transverse axis of the time series data display screen is set as the time axis, and a longitudinal axis thereof is set as the data array axis,
wherein in the three-dimensional display mode, the rotation axis and the longitudinal axis coincides with each other,
wherein the time series data display screen includes two time axes of a first time axis which is two-dimensionally displayed similar to the two-dimensional display mode even in the three-dimensional display mode, and a second time axis which is provided in the two-dimensional plane on which the time series data is displayed and is three-dimensionally displayed similar to the two-dimensional plane, and
wherein a display period of the first time axis is changed in conjunction with a display period of the second time axis which is changed depending on the rotation angle of the two-dimensional plane.

16. A time series data display control system comprising:
a processor configured to execute:
a screen data generating unit that generates a time series data display screen on which a plurality of pieces of time series data are displayed; and
a screen display control unit that performs switching between display modes of the time series data display screen, in which the display modes include two display modes of a two-dimensional display mode in which the time series data is displayed on a two-dimensional plane formed by two axes of a time axis of the plurality of pieces of time series data and a data array axis orthogonal to the time axis, on which the plurality of pieces of time series data are arrayed, and a three-dimensional display mode in which a time scale is set to be longer than a time axis of the two-dimensional display mode and the two-dimensional plane on which the time series data is displayed is three-dimensionally displayed using the laws of perspective by which a plurality of straight lines parallel to the time axis in the two-dimensional display mode are drawn to be converged toward the past on the time axis wherein the three-dimensional display mode is a display mode in which the two-dimensional plane in the two-dimensional display mode is virtually rotated around a rotation axis orthogonal to the time axis, and wherein in the three-dimensional display mode, a part of a display period of the time series data is able to be two-dimensionally displayed, wherein a rotation angle of the two-dimensional plane is changeable, wherein the time scale of the time axis becomes longer as the rotation angle becomes larger, wherein in the two-dimensional display mode, a transverse axis of the time series data display screen is set as the time axis, and a longitudinal axis thereof is set as the data array axis, wherein in the three-dimensional display mode, the rotation axis and the longitudinal axis coincides with each other, wherein the time series data display screen includes two time axes of a first time axis which is two-dimensionally displayed similar to the two-dimensional display mode even in the three-dimensional display mode, and a second time axis which is provided in the two-dimensional plane on which the time series data is displayed and is three-dimensionally displayed similar to the two-dimensional plane, and wherein a display period of the first time axis is changed in conjunction with a display period of the second time axis which is changed depending on the rotation angle of the two-dimensional plane.

* * * * *